(12) United States Patent
Schlingloff et al.

(10) Patent No.: US 7,291,584 B2
(45) Date of Patent: Nov. 6, 2007

(54) USE OF METAL COMPLEX COMPOUNDS AS OXIDATION CATALYSTS

(75) Inventors: Gunther Schlingloff, Riehen (CH); Torsten Wieprecht, Schopfheim (DE); Uwe Heinz, Saarlouis (DE); Albert Schneider, Grenzach-Wyhlen (DE); Marie-Josée Dubs, Wittersdorf (FR); Frank Bachmann, Freiburg (DE); Menno Hazenkamp, Riehen (CH); Thomas Ehlis, Freiburg (DE); Cornelia Vincenzi, Schopfheim (DE); Josef Dannacher, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/520,398

(22) Filed: Sep. 13, 2006

(65) Prior Publication Data

US 2007/0032656 A1    Feb. 8, 2007

Related U.S. Application Data

(62) Division of application No. 10/531,906, filed as application No. PCT/EP03/11636 on Oct. 21, 2003, now Pat. No. 7,138,363.

(30) Foreign Application Priority Data

Oct. 30, 2002    (EP) .................... 02405929

(51) Int. Cl.
C11D 3/20    (2006.01)
C11D 3/26    (2006.01)
C11D 3/28    (2006.01)
C11D 3/37    (2006.01)

(52) U.S. Cl. ............... 510/376; 510/303; 510/349; 510/357; 510/311; 510/475; 510/477; 510/495; 510/500; 510/505; 510/506; 252/186.26; 252/186.27; 252/186.39; 502/200; 502/324; 502/325; 544/245

(58) Field of Classification Search ............... None
See application file for complete search history.

(56) References Cited

U.S. PATENT DOCUMENTS

| | | | |
|---|---|---|---|
| 5,362,421 A | 11/1994 | Kropp et al. | 252/512 |
| 5,453,450 A | 9/1995 | Kinzer et al. | 522/18 |
| 6,245,115 B1 | 6/2001 | Appel et al. | 8/111 |
| 6,617,299 B1 | 9/2003 | Carina et al. | 510/302 |

FOREIGN PATENT DOCUMENTS

| | | |
|---|---|---|
| WO | 00/60043 | 10/2000 |
| WO | WO02/088289 | * 11/2002 |

OTHER PUBLICATIONS

The Preparation and Properties of Certain Pyridylprimidines and Bidiazines as Potential Chelating Agents for Iron(II), Lafferty et al, 1591-1596, Oct. 7, 1966.*
Lafferty et al., J. Org. Chem., vol. 32, No. 5, (1967), pp. 1591-1596.

* cited by examiner

Primary Examiner—Gregory R. Del Cotto
(74) Attorney, Agent, or Firm—Mervin G. Wood; Tyler A. Stevenson

(57) ABSTRACT

Use of metal complex compounds of formula (1) and/or (1')

$$[L_nMe_mX_p]^zY_q, \quad (1)$$

$$[L'_nMe_mX_p]^zY_q, \quad (1')$$

wherein all substituents are as defined in the claims, as catalysts for oxidation reactions, and also novel metal complex compounds and novel ligands.

6 Claims, No Drawings

USE OF METAL COMPLEX COMPOUNDS AS OXIDATION CATALYSTS

This application is a divisional of application Ser. No. 10/531,906, now U.S. Pat. No. 7,138,363, which is a 371 of international app. No. PCT/EP0311636, filed Oct. 21, 2003, the contents of which are hereby incorporated by reference.

The present invention relates to the use, as oxidation catalysts, of metal complex compounds having pyrimidine or triazinebispyrimidine ligands or mixtures of such ligands. The present invention relates also to formulations comprising such metal complex compounds, to novel metal complex compounds and to novel ligands.

The metal complex compounds are used especially for enhancing the action of peroxides, for example in the treatment of textile material, without at the same time causing any appreciable damage to fibres and dyeings.

The metal complex compounds may also be used as catalysts for oxidation using molecular oxygen and/or air, that is, without peroxide compounds and/or peroxide-forming substances.

Peroxide-containing bleaching agents have long been used in washing and cleaning processes. They have an excellent action at a liquor temperature of 90° C. and above, but their performance noticeably decreases with lower temperatures. Various transition metal ions added in the form of suitable salts, and coordination compounds containing such cations are known to activate $H_2O_2$. In that manner it is possible for the bleaching effect, which is unsatisfactory at lower temperatures, of $H_2O_2$ or precursors that release $H_2O_2$ and of other peroxo compounds, to be increased. There are important for practical purposes, in that respect, especially combinations of transition metal ions and ligands of which the peroxide activation is manifested in an increased tendency towards oxidation in relation to substrates and not only in a catalase-like disproportionation. The latter activation, which in the present case tends rather to be undesirable, could even impair the bleaching effects, which are inadequate at low temperatures, of $H_2O_2$ and its derivatives In terms of $H_2O_2$ activation having effective bleaching action, mononuclear and polynuclear variants of manganese complexes having various ligands, especially 1,4,7-trimethyl-1,4,7-triazacyclononane and optionally oxygen-containing bridging ligands, are currently regarded as being especially effective. Such catalysts are adequately stable under practical conditions and, with $Mn^{n+}$, contain an ecologically acceptable metal cation, but their use is unfortunately associated with considerable damage to dyes and fibres.

The aim of the present invention was accordingly to provide improved metal complex catalysts for oxidation processes that meet the above requirements and, especially, enhance the action of peroxide compounds in the most varied fields of application without causing any appreciable damage.

The invention accordingly relates to the use, as a catalyst for oxidation reactions, of at least one metal complex of formula (1)

$$[L_nMe_mX_p]^zY_q \qquad (1),$$

wherein Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge of Y), and
L is a ligand of formula (2)

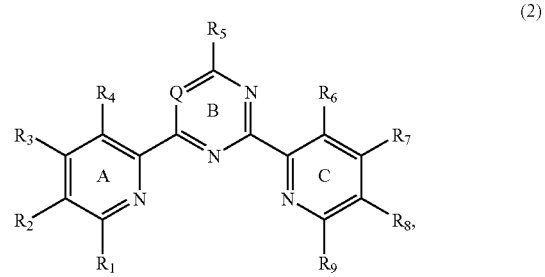

wherein
Q is N or $CR_{10}$,
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$ wherein
$R_{11}$ is in each case hydrogen, a cation or unsubstituted or substituted $C_1$-$C_{18}$alkyl or unsubstituted or substituted aryl; —$SR_{12}$, —$SO_2R_{12}$ or —$OR_{12}$ wherein
$R_{12}$ is in each case hydrogen or unsubstituted or substituted $C_1$-$C_{18}$alkyl or unsubstituted or substituted aryl; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—$N$—$R_{13}R_{14}$ or —$N(R_{12})$—$N^{\oplus}R_{13}R_{14}R_{15}$, wherein
$R_{12}$ is as defined above and
$R_{13}$, $R_{14}$ and $R_{15}$ are each independently of the other(s) hydrogen or unsubstituted or substituted $C_1$-$C_{18}$alkyl or unsubstituted or substituted aryl, or
$R_{13}$ and $R_{14}$, together with the nitrogen atom linking them, form an unsubstituted or substituted 5-, 6- or 7-membered ring which may contain further hetero atoms.

A specific use as a catalyst is in relation to oxidation using molecular oxygen and/or air.

Suitable substituents for the alkyl groups, aryl groups, alkylene groups or 5-, 6- or 7-membered rings are especially $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or phenoxy or naphthyloxy.

The $C_1$-$C_{18}$alkyl radicals mentioned for the compounds of formula (2) are, for example, straight-chain or branched alkyl radicals, such as methyl, ethyl, n-propl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkylradicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formula (2) are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1$-$C_4$alkyl, $C_1$-$C_4$alkoxy, phenyl and hydroxy. Special preference is given to the corresponding phenyl radicals.

The $C_1$-$C_6$alkylene groups mentioned for the compounds of formula (2) are, for example, straight-chain or branched alkylene radicals, such as methylene, ethylene, n-propylene or n-butylene. $C_1$-$C_4$Alkylene groups are preferred. The alkylene radicals mentioned may be unsubstituted or substituted, for example by hydroxy or $C_1$-$C_4$alkoxy.

In the compounds of formulae (1) and (2), halogen is preferably chlorine, bromine or fluorine, with special preference being given to chlorine.

Examples of cations that come into consideration for compounds of formulae (1) and (2) include alkali metal cations, such as lithium, potassium and especially sodium, alkaline earth metal cations, such as magnesium and calcium, and ammonium cations. The alkali metal cations, especially sodium, are preferred.

Suitable metal ions for Me for the compounds of formula (1) are, for example, manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt II-III, nickel II-III and copper II-III, especially iron II-IV.

For the radical X for the compounds of formula (1) there come into consideration, for example, $CH_3CN$; $H_2O$; $F^{31}$; $Cl^-$; $Br^-$; $HOO^-$; $O_2^{2-}$; $O^{2-}$; $R_{16}COO^-$; $R_{16}O^-$; $LMeO^-$ and $LMeOO^-$, wherein $R_{16}$ is hydrogen, —$SO_3C_1$-$C_4$alkyl or unsubstituted or substituted $C_1$-$C_{18}$alkyl or unsubstituted or substituted aryl, and $C_1$-$C_{18}$alkyl, aryl, L and Me have the definitions and preferred meanings given hereinabove and hereinbelow. Especially preferably, $R_{16}$ is hydrogen; $C_1$-$C_4$alkyl; sulfophenyl or phenyl, especially hydrogen.

As counter-ion Y for the compounds of formula (1) there come into consideration, for example, $R_{17}COO^-$; $ClO_4^-$; $BF_4^-$; $PF_6^-$; $R_{17}SO_3^-$; $R_{17}SO_4^-$; $SO_4^{2-}$; $NO_3^-$; $F^{31}$; $Cl^-$; $Br^-$ and $I^-$, wherein $R_{17}$ is hydrogen or unsubstituted or substituted $C_1$-$C_{18}$alkyl or unsubstituted or substituted aryl. $R_{17}$ as $C_1$-$C_{18}$alkyl or aryl has the definitions and preferred meanings given hereinabove and hereinbelow. Especially preferably, $R_{17}$ is hydrogen; $C_1$-$C_4$alkyl; phenyl or sulfophenyl, especially hydrogen or 4-sulfophenyl. The charge of the counter-ion Y is accordingly preferably 1- or 2-, especially 1-.

Y can also be a customary organic counter-ion, for example citrate, oxalate or tartrate.

For the compounds of formula (1), n is preferably an integer having a value of from 1 to 4, preferably 1 or 2 and especially 1.

For the compounds of formula (1), m is preferably an integer having a value of 1 or 2, especially 1.

For the compounds of formula (1), p is preferably an integer having a value of from 0 to 4, especially 2.

For the compounds of formula (1), z is preferably an integer having a value of from 8– to 8+, especially from 4– to 4+ and especially preferably from 0 to 4+. z is more especially the number 0.

For the compounds of formula (1), q is preferably an integer from 0 to 8, especially from 0 to 4, and is especially preferably the number 0.

$R_{11}$ in compounds of formula (2) is preferably hydrogen, a cation, $C_1$-$C_{12}$alkyl, unsubstituted phenyl or phenyl substituted as indicated above. Especially preferably, $R_{11}$ is hydrogen, an alkali metal cation, alkaline earth metal cation or ammonium cation, $C_1$-$C_4$alkyl or phenyl, especially hydrogen or an alkali metal cation, alkaline earth metal cation or ammonium cation.

$R_{12}$ in compounds of formula (2) is preferably hydrogen, $C_1$-$C_{12}$alkyl, unsubstituted phenyl or phenyl substituted as indicated above. Especially preferably, $R_{12}$ is hydrogen, $C_1$-$C_4$alkyl or phenyl, more especially hydrogen or $C_1$-$C_4$alkyl, preferably hydrogen. Examples of the radical of formula —$OR_{12}$ that may be mentioned are hydroxy and $C_1$-$C_4$alkoxy, such as methoxy and especially ethoxy.

When $R_{13}$ and $R_{14}$ in compounds of formula (2), together with the nitrogen atom linking them, form a 5-, 6- or 7-membered ring, that ring is preferably an unsubstituted or $C_1$-$C_4$alkyl-substituted pyrrolidine, piperidine, piperazine, morpholine or azepane ring, wherein the amino groups may be quaternised, in which case preferably the nitrogen atoms that are not bonded directly to one of the three rings A, B or C are quaternised.

The piperazine ring may, for example, be substituted by one or two unsubstituted $C_1$-$C_4$alkyl and/or substituted $C_1$-$C_4$alkyl at the nitrogen atom not bonded to the pyridine ring. In addition, $R_{13}$, $R_{14}$ and $R_{15}$ are preferably hydrogen, unsubstituted or hydroxy-substituted $C_1$-$C_{12}$alkyl, unsubstituted phenyl or phenyl substituted as indicated above. Special preference is given to hydrogen, unsubstituted or hydroxy-substituted $C_1$-$C_4$alkyl or unsubstituted or hydroxy-substituted phenyl, especially hydrogen or unsubstituted or hydroxy-substituted $C_1$-$C_4$alkyl, preferably hydrogen.

Preference is given to ligands L of formula (2) wherein $R_5$ is not hydrogen.

$R_5$ in L of formula (2) is preferably $C_1$-$C_{12}$alkyl; phenyl unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthyloxy; cyano; halogen; nitro; —$COOR_{11}$ or —$SO_3R_{11}$ wherein $R_{11}$ is in each case hydrogen, a cation, $C_1$-$C_{12}$alkyl, unsubstituted phenyl or phenyl substituted as indicated above; —$SR_{12}$, —$SO_2R_{12}$ or —$OR_{12}$ wherein $R_{12}$ is in each case hydrogen, $C_1$-$C_{12}$alkyl, unsubstituted phenyl or phenyl substituted as indicated above; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N(R_{12})$—($C_1$-$C_6$alkylene)—$N^{\oplus}R_{13}R_{14}R_{15}$; —$N(R_{12})$—N—$R_{13}R_{14}$ or —$N(R_{12})$—$N^{\oplus}R_{13}R_{14}R_{15}$, wherein $R_{12}$ may have one of the meanings given above and $R_{13}$, $R_{14}$ and $R_{15}$ are each independently of the other(s) hydrogen, unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring unsubstituted or substituted by at least one unsubstituted $C_1$-$C_4$alkyl and/or substituted $C_1$-$C_4$alkyl, wherein the nitrogen atom may be quaternised.

$R_5$ in L of formula (2) is especially preferably phenyl unsubstituted or substituted by $C_1$-$C_4$alkyl, $C_1$-$C_4$alkoxy, halogen, phenyl or by hydroxy; cyano; nitro; —$COOR_{11}$ or —SO$_3$R$_{11}$ wherein R$_{11}$ is in each case hydrogen, a cation, C$_1$-C$_4$alkyl or phenyl; —SR$_{12}$, —SO$_2$R$_{12}$ or —OR$_{12}$ wherein R$_{12}$ is in each case hydrogen, C$_1$-C$_4$alkyl or phenyl; —N(CH$_3$)—NH$_2$ or —NH—NH$_2$; amino; N-mono- or N,N-di-C$_1$-C$_4$alkylamino unsubstituted or substituted by hydroxy in the alkyl moiety; or an unsubstituted or C$_1$-C$_4$alkyl-substituted pyrrolidine, piperidine, piperazine, morpholine or azepane ring.

R$_5$ in L of formula (2) is very especially preferably C$_1$-C$_4$alkoxy; hydroxy; phenyl unsubstituted or substituted by C$_1$-C$_4$alkyl, C$_1$-C$_4$alkoxy, phenyl or by hydroxy; hydrazine; amino; N-mono- or N,N-di-C$_1$-C$_4$alkylamino unsubstituted or substituted by hydroxy in the alkyl moiety; or an unsubstituted or C$_1$-C$_4$alkyl-substituted pyrrolidine, piperidine, piperazine, morpholine or azepane ring.

As radicals R$_5$ in L of formula (2) there are especially important C$_1$-C$_4$alkoxy; hydroxy; hydrazine; amino; N-mono- or N,N-di-C$_1$-C$_4$alkylamino unsubstituted or substituted by hydroxy in the alkyl moiety; and an unsubstituted or C$_1$-C$_4$alkyl-substituted pyrrolidine, piperidine, piperazine, morpholine or azepane ring.

As radicals R$_5$ in L of formula (2) there are very especially important C$_1$-C$_4$alkoxy; hydroxy; N-mono- or N,N-di-C$_1$-C$_4$alkylamino substituted by hydroxy in the alkyl moiety; and an unsubstituted or C$_1$-C$_4$alkyl-substituted pyrrolidine, piperidine, piperazine, morpholine or azepane ring. Of those, hydroxy is of special interest.

The preferred meanings given above for R$_5$ apply also to R$_1$, R$_2$, R$_3$, R$_4$, R$_6$, R$_7$, R$_8$, R$_9$ and R$_{10}$ in L of formula (2), but those radicals may additionally be hydrogen.

According to one embodiment of the present invention, R$_1$, R$_2$, R$_3$, R$_4$, R$_6$, R$_7$, R$_8$, R$_9$ and R$_{10}$ in L of formula (2) are hydrogen and R$_5$ in L of formula (2) is a radical other than hydrogen having the definition and preferred meanings indicated above.

According to a further embodiment of the present invention, R$_1$, R$_2$, R$_4$, R$_6$, R$_8$, R$_9$ and R$_{10}$ in L of formula (2) are hydrogen and R$_3$, R$_5$ and R$_7$ in L of formula (2) are radicals other than hydrogen, for each of which the definition and preferred meanings indicated above for R$_5$ apply.

Preferred as ligands L are those of formula (3a) and/or (3b)

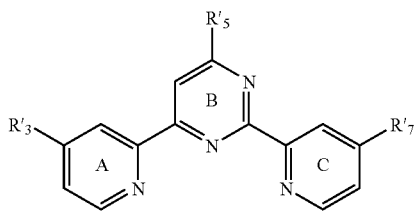

(3a)

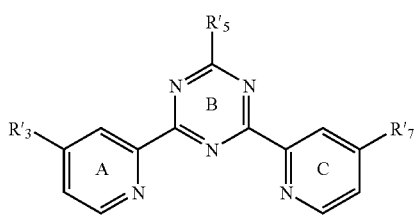

(3b)

wherein R'$_3$ and R'$_7$ have the definitions and preferred meanings indicated above for R$_3$ and R$_7$, and R'$_5$ has the definition and preferred meanings indicated above for R$_5$.

Especially preferred as ligands L are those of formula (3a) and/or (3b)

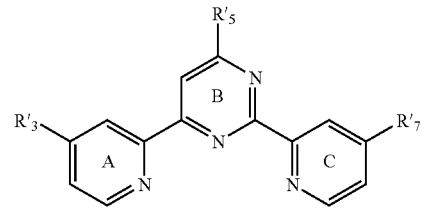

(3a)

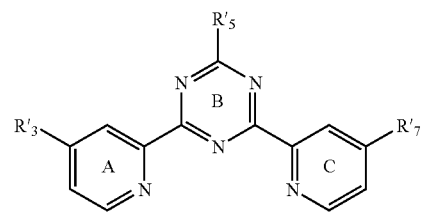

(3b)

wherein

R'$_5$ is C$_1$-C$_4$alkoxy; hydroxy; N-mono- or N,N-di-C$_1$-C$_4$alkylamino unsubstituted or substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein R$_{12}$ is hydrogen; C$_1$-C$_{12}$alkyl or unsubstituted phenyl or phenyl substituted by (substituted in the alkyl moiety by hydroxy) N-mono- or N,N-di-C$_1$-C$_4$alkylamino-, N-phenylamino-, N-naphthylamino-, phenyl-, phenoxy- or naphthyloxy, and R$_{13}$ and R$_{14}$ are each independently of the other hydrogen, unsubstituted or hydroxy-substituted C$_1$-C$_{12}$alkyl, unsubstituted phenyl or phenyl substituted as indicated above, or R$_{13}$ and R$_{14}$, together with the nitrogen atom linking them, form a pyrrolidine, piperidine, piperazine, morpholine or azepane ring that is unsubstituted or substituted by at least one unsubstituted C$_1$-C$_4$alkyl and/or substituted C$_1$-C$_4$alkyl, especially a pyrrolidine, piperidine, piperazine, morpholine or azepane ring, and R'$_3$ and R'$_7$ are each independently of the other hydrogen; C$_1$-C$_4$alkoxy; hydroxy; N-mono- or N,N-di-C$_1$-C$_4$alkylamino substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein R$_{12}$ is hydrogen; C$_1$-C$_{12}$alkyl or unsubstituted phenyl or phenyl substituted by (substituted in the alkyl moiety by hydroxy) N-mono- or N,N-di-C$_1$-C$_4$alkylamino-, N-phenylamino-, N-naphthylamino-, phenyl-, phenoxy- or naphthyloxy, and R$_{13}$ and R$_{14}$ are each independently of the other hydrogen; unsubstituted or hydroxy-substituted C$_1$-C$_{12}$alkyl, unsubstituted phenyl or phenyl substituted as indicated above, or R$_{13}$ and R$_{14}$, together with the nitrogen atom linking them, form a pyrrolidine, piperidine, piperazine, morpholine or azepane ring that is unsubstituted or substituted by at least one unsubstituted C$_1$-C$_4$alkyl and/or substituted $C_1-C_4$alkyl, especially a pyrrolidine, piperidine, piperazine, morpholine or azepane ring.

An embodiment of the invention to which preference is likewise given is the use, as a catalyst for oxidation reactions, of at least one metal complex compound of formula (1')

wherein
Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge of Y), and
L' is a ligand of formula (2')

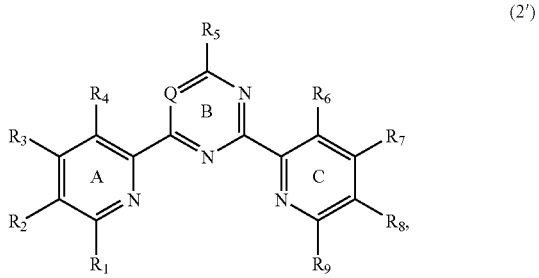

wherein
Q is N or $CR_{10}$,
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1-C_{18}$alkyl or unsubstituted or substituted aryl; cyano; halogen; nitro; —$COOR_{11}$ or —$SO_3R_{11}$ wherein
$R_{11}$ is in each case hydrogen, a cation or unsubstituted or substituted $C_1-C_{18}$alkyl or unsubstituted or substituted aryl; —$SR_{12}$, —$SO_2R_{12}$ or —$OR_{12}$ wherein
$R_{12}$ is in each case hydrogen or unsubstituted or substituted $C_1-C_{18}$alkyl or unsubstituted or substituted aryl; —$NR_{13}R_{14}$; —($C_1-C_6$alkylene)—$NR_{13}R_{14}$; —$N^{\oplus}R_{13}R_{14}R_{15}$; —($C_1-C_6$alkylene)—$N^{\oplus}R_{13}R_{14}R_{15}$; —$N(R_{12})$—($C_1-C_6$alkylene)—$NR_{13}R_{14}$; —$N[(C_1-C_6$alkylene)—$NR_{13}R_{14}]_2$; —$N(R_{12})$—($C_1-C_6$alkylene)—$N^{\oplus}R_{13}R_{14}R_{15}$; —$N[(C_1-C_6$alkylene)—$N^{\oplus 61}R_{13}R_{14}R_{15}]_2$; —$N(R_{12})$—N—$R_{13}R_{14}$ or —$N(R_{12})$—$N^{\oplus}R_{13}R_{14}R_{15}$, wherein
$R_{12}$ is as defined above and
$R_{13}$, $R_{14}$ and $R_{15}$ are each independently of the other(s) hydrogen or unsubstituted or substituted $C_1-C_{18}$alkyl or unsubstituted or substituted aryl, or
$R_{13}$ and $R_{14}$, together with the nitrogen atom linking them, form an unsubstituted or substituted 5-, 6- or 7-membered ring which may contain further hetero atoms, with the proviso that
at least one of the substituents $R_1$ to $R_{10}$ contains a quaternised nitrogen atom that is not bonded directly to one of the three rings A, B and/or C.

Suitable substituents for the alkyl groups, aryl groups, alkylene groups or 5-, 6- or 7-membered rings are especially $C_1-C_4$alkyl; $C_1-C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino; phenyl; phenoxy and naphthyloxy.

The $C_1-C_{18}$alkyl radicals mentioned for the compounds of formula (2') are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1-C_{12}$alkyl radicals, especially $C_1-C_8$alkyl radicals and preferably $C_1-C_4$alkyl radicals. The mentioned alkyl radicals may be unsubstituted or substituted e.g. by hydroxy, $C_1-C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formula (2') are phenyl or naphthyl each unsubstituted or substituted by $C_1-C_4$alkyl, $C_1-C_4$alkoxy, halogen, cyano, nitro, carboxy, sulfo, hydroxy, amino, N-mono- or N,N-di-$C_1-C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1-C_4$alkyl, $C_1-C_4$alkoxy, phenyl and hydroxy. Special preference is given to the corresponding phenyl radicals.

The $C_1-C_6$alkylene groups mentioned for the compounds of formula (2') are, for example, straight-chain or branched alkylene radicals, such as methylene, ethylene, n-propylene or n-butylene. $C_1-C_4$Alkylene groups are preferred. The alkylene radicals mentioned may be unsubstituted or substituted, for example by hydroxy or $C_1-C_4$alkoxy.

In the compounds of formulae (1') and (2'), halogen is preferably chlorine, bromine or fluorine, with special preference being given to chlorine.

Examples of cations that come into consideration for compounds of formulae (1') and (2') include alkali metal cations, such as lithium, potassium and especially sodium, alkaline earth metal cations, such as magnesium and calcium, and ammonium cations. The alkali metal cations, especially sodium, are preferred.

Suitable metal ions for Me for the compounds of formula (1') are, for example, manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt II-III, nickel II-III and copper II-III, especially iron II-IV.

For the radical X for the compounds of formula (1') there come into consideration, for example, $CH_3CN$, $H_2O$, $F^{31}$, $Cl^-$, $Br^-$, $HOO^-$, $O_2^{2-}$, $O^{2-}$, $R_{16}COO^-$, $R_{16}O^-$, $LMeO^-$ and $LMeOO^-$, wherein $R_{16}$ is hydrogen, —$SO_3C_1-C_4$alkyl or unsubstituted or substituted $C_1-C_{18}$alkyl or unsubstituted or substituted aryl, and $C_1-C_{18}$alkyl, aryl, L and Me have the definitions and preferred meanings given hereinabove and hereinbelow. Especially preferably, $R_{16}$ is hydrogen; $C_1-C_4$alkyl; sulfophenyl or phenyl, especially hydrogen.

As counter-ion Y for the compounds of formula (1') there come into consideration, for example, $R_{17}COO^-$, $ClO_4^-$, $BF_4^-$, $PF_6^-$, $R_{17}SO_3^-$, $R_{17}SO_4^-$, $SO_4^{2-}$, $NO_3^-$, $F^{31}$, $Cl^-$, $Br^-$ and $I^-$, wherein $R_{17}$ is hydrogen or unsubstituted or substituted $C_1-C_{18}$alkyl or unsubstituted or substituted aryl. $R_{17}$ as $C_1$-$C_{18}$alkyl or aryl has the definitions and preferred meanings given hereinabove and hereinbelow. Especially preferably, $R_{17}$ is hydrogen; $C_1$-$C_4$alkyl; phenyl or sulfophenyl, especially hydrogen or 4-sulfophenyl. The charge of the counter-ion Y is accordingly preferably 1- or 2-, especially 1-.

Y can also be a customary organic counter-ion, for example citrate, oxalate or tartrate.

For the compounds of formula (1'), n is preferably an integer having a value of from 1 to 4, preferably 1 or 2 and especially 1.

For the compounds of formula (1'), m is preferably an integer having a value of 1 or 2, especially 1.

For the compounds of formula (1'), p is preferably an integer having a value of from 0 to 4, especially 2.

For the compounds of formula (1'), z is preferably an integer having a value of from 8– to 8+, especially from 4– to 4+ and especially preferably from 0 to 4+. z is more especially the number 0.

For the compounds of formula (1'), q is preferably an integer from 0 to 8, especially from 0 to 4, and is especially preferably the number 0.

$R_{11}$ in compounds of formula (2') is preferably hydrogen, a cation, $C_1$-$C_{12}$alkyl, unsubstituted phenyl or phenyl substituted as indicated above. Especially preferably, $R_{11}$ is hydrogen, an alkali metal cation, alkaline earth metal cation or ammonium cation, $C_1$-$C_4$alkyl or phenyl, especially hydrogen or an alkali metal cation, alkaline earth metal cation or ammonium cation.

$R_{12}$ in compounds of formula (2') is preferably hydrogen, $C_1$-$C_{12}$alkyl, unsubstituted phenyl or phenyl substituted as indicated above. Especially preferably, $R_{12}$ is hydrogen, $C_1$-$C_4$alkyl or phenyl, especially hydrogen or $C_1$-$C_4$alkyl, preferably hydrogen. Examples of the radical of formula —$OR_{12}$ that may be mentioned are hydroxy and $C_1$-$C_4$alkoxy, such as methoxy and especially ethoxy.

When $R_{13}$ and $R_{14}$ in compounds of formula (2'), together with the nitrogen atom linking them, form a 5-, 6- or 7-membered ring, that ring is preferably an unsubstituted or $C_1$-$C_4$alkyl-substituted pyrrolidine, piperidine, piperazine, morpholine or azepane ring, wherein the amino groups may be quaternised, in which case preferably the nitrogen atoms that are not bonded directly to one of the three rings A, B or C are quaternised.

The piperazine ring may, for example, be substituted by one or two unsubstituted $C_1$-$C_4$alkyl and/or substituted $C_1$-$C_4$alkyl at the nitrogen atom not bonded to the pyridine ring. In addition, $R_{13}$, $R_{14}$ and $R_{15}$ are preferably hydrogen, unsubstituted or hydroxy-substituted $C_1$-$C_{12}$alkyl, unsubstituted phenyl or phenyl substituted as indicated above. Special preference is given to hydrogen, unsubstituted or hydroxy-substituted $C_1$-$C_4$alkyl, or phenyl, especially hydrogen or unsubstituted or hydroxy-substituted $C_1$-$C_4$alkyl, preferably hydrogen.

Preference is given to ligands L' of formula (2') wherein $R_5$ is not hydrogen.

Preference is given to ligands L' of formula (2') wherein $R_5$ is preferably phenyl unsubstituted or substituted by $C_1$-$C_4$alkyl, $C_1$-$C_4$alkoxy, halogen, phenyl or by hydroxy; cyano; nitro; —$COOR_{11}$ or —$SO_3R_{11}$ wherein $R_{11}$ is in each case hydrogen, a cation, $C_1$-$C_4$alkyl or phenyl; —$SR_{12}$, —$SO_2R_{12}$ or —$OR_{12}$ wherein $R_{12}$ is in each case hydrogen, $C_1$-$C_4$alkyl or phenyl; —$N(CH_3)$—$NH_2$ or —$NH$—$NH_2$; amino; N-mono- or N,N-di-$C_1$-$C_4$alkylamino unsubstituted or substituted by hydroxy in the alkyl moiety, wherein the nitrogen atoms, especially the nitrogen atoms not bonded to one of the three rings A, B or C, may be quaternised; N-mono- or N,N-di-$C_1$-$C_4$alkyl-$N^\oplus R_{13}R_{14}R_{15}$ unsubstituted or substituted by hydroxy in the alkyl moiety, wherein $R_{13}$, $R_{14}$ and $R_{15}$ are each independently of the others hydrogen or unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, morpholine or azepane ring unsubstituted or substituted by at least one $C_1$-$C_4$alkyl or by at least one unsubstituted $C_1$-$C_4$alkyl and/or substituted $C_1$-$C_4$alkyl, wherein the nitrogen atom may be quaternised; N-mono- or N,N-di-$C_1$-$C_4$alkyl-$NR_{13}R_{14}$ unsubstituted or substituted by hydroxy in the alkyl moiety, wherein $R_{13}$ and $R_{14}$ may be as defined above.

$R_5$ in L' of formula (2') is very especially $C_1$-$C_4$alkoxy; hydroxy; phenyl unsubstituted or substituted by $C_1$-$C_4$alkyl, $C_1$-$C_4$alkoxy, phenyl or by hydroxy; hydrazine; amino; N-mono- or N,N-di-$C_1$-$C_4$alkylamino unsubstituted or substituted by hydroxy in the alkyl moiety, wherein the nitrogen atoms, especially the nitrogen atoms not bonded to one of the three rings A, B or C, may be quaternised; or a pyrrolidine, piperidine, morpholine or azepane ring unsubstituted or substituted by one or two unsubstituted $C_1$-$C_4$alkyl and/or substituted $C_1$-$C_4$alkyl, wherein the nitrogen atom may be quaternised;

A likewise very especially preferred radical that may be mentioned for $R_5$ in L' of formula (2') is

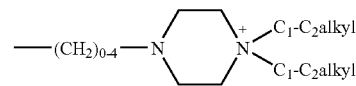

wherein the ring, the alkylene group and the two alkyl groups may additionally independently from each other be substituted.

As radicals $R_5$ in L' of formula (2'), there are especially important $C_1$-$C_4$alkoxy; hydroxy; hydrazine; amino; N-mono- or N,N-di-$C_1$-$C_4$alkylamino unsubstituted or substituted by hydroxy in the alkyl moiety, wherein the nitrogen atoms, especially the nitrogen atoms not bonded to one of the three rings A, B or C, may be quaternised; or a pyrrolidine, piperidine, piperazine, morpholine or azepane ring unsubstituted or substituted by at least one $C_1$-$C_4$alkyl, wherein the nitrogen atoms may be quaternised.

As a further, especially important example of $R_5$ in L' of formula (2') the following radical may be mentioned:

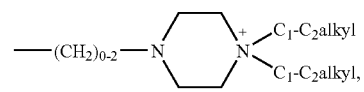

wherein the ring, the alkylene group and the two alkyl groups may additionally independently from each other substituted.

As radicals $R_5$ in L' of formula (2'), there are especially important $C_1$-$C_4$alkoxy; hydroxy; N-mono- or N,N-di-$C_1$-$C_4$alkylamino substituted by hydroxy in the alkyl moiety, wherein the nitrogen atoms, especially the nitrogen atoms not bonded to one of the three rings A, B or C, may be quaternised; or a pyrrolidine, piperidine, morpholine or azepane ring unsubstituted or substituted by at least one$C_1$-$C_4$alkyl, wherein the amino groups may be quaternised.

As examples of the radical $R_5$ in L' of formula (2') mention may be made especially of —OH;

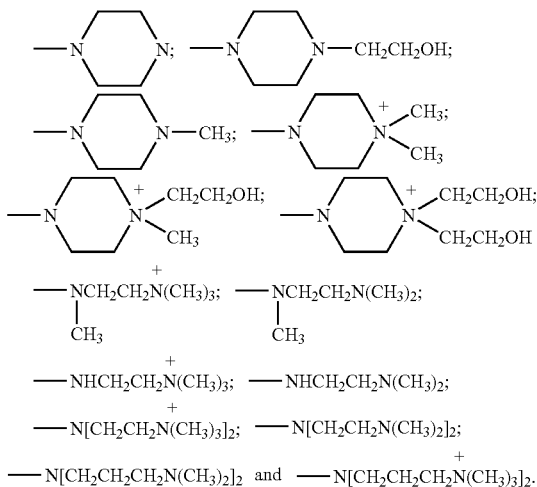

Of those, hydroxy is of special interest.

The preferred meanings given above for $R_5$ in L' of formula (2') apply also to $R_1$, $R_2$, $R_3$, $R_4$, $R_6$, $R_7$, $R_8$, $R_9$ and $R_{10}$ in L' of formula (2'), but those radicals may additionally be hydrogen.

In accordance with one embodiment of the present invention, $R_1$, $R_2$, $R_3$, $R_4$, $R_6$, $R_7$, $R_8$, $R_9$ and $R_{10}$ in L' of formula (2') are hydrogen and $R_5$ in L' of formula (2') is a radical other than hydrogen having the definition and preferred meanings indicated above.

In accordance with a further embodiment of the present invention, $R_1$, $R_2$, $R_3$, $R_4$, $R_6$, $R_7$, $R_8$, $R_9$ and $R_{10}$ in L' of formula (2') are hydrogen and $R_3$, $R_5$ and $R_7$ in L' of formula (2') are radicals other than hydrogen having the definitions and preferred meanings indicated above for $R_5$.

A likewise preferred use according to the invention of at least one metal complex compound of formula (1') as a catalyst for oxidation reactions is the use of such a compound wherein at least one of the substituents $R_1$ to $R_{10}$ in L' of formula (2'), preferably $R_3$, $R_5$ and/or $R_7$, is one of the following radicals: —($C_1$-$C_6$alkylene)—$N^{\oplus}R_{13}R_{14}R_{15}$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—$N^{\oplus}R_{13}R_{14}R_{15}$, wherein $R_{12}$ is as defined above and $R_{13}$, $R_{14}$ and $R_{15}$ are each independently of the others hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms; or —$NR_{13}R_{14}$; —($C_1$-$C_6$alkylene)—$NR_{13}R_{14}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—N—$R_{13}R_{14}$ wherein $R_{12}$ and $R_{15}$ are as defined above and $R_{13}$ and $R_{14}$, together with the nitrogen atom linking them, form a 5-, 6- or 7-membered ring which is unsubstituted or substituted by at least one unsubstituted $C_1$-$C_4$alkyl and/or substituted $C_1$-$C_4$alkyl and may contain further hetero atoms, wherein at least one nitrogen atom not bonded to one of three rings A, B and/or C is quaternised. A likewise more preferred use according to the invention of at least one metal complex compound of formula (1') as a catalyst for oxidation reactions is the use of such a compound wherein at least one of the substituents $R_1$ to $R_{10}$ in L', preferably $R_3$, $R_5$ and/or $R_7$, is one of the following radicals: —($C_1$-$C_4$alkylene)—$N^{\oplus}R_{13}R_{14}R_{15}$; —$N(R_{12})$—($C_1$-$C_4$alkylene)—$N^{\oplus}R_{13}R_{14}R_{15}$; —$N[(C_1$-$C_4$alkylene)—$N^{\oplus}R_{13}R_{14}R_{15}]_2$; —$N(R_{12})$—$N^{\oplus}R_{13}R_{14}R_{15}$, wherein $R_{12}$ is hydrogen, unsubstituted or substituted $C_1$-$C_{12}$alkyl or unsubstituted or substituted aryl and $R_{13}$, $R_{14}$ and $R_{15}$ are each independently of the others hydrogen or unsubstituted or substituted $C_1$-$C_{12}$alkyl or unsubstituted or substituted aryl, or $R_{13}$ and $R_{14}$, together with the nitrogen atom linking them, form a 5-, 6- or 7-membered ring which is unsubstituted or substituted by at least one unsubstituted $C_1$-$C_4$alkyl and/or substituted $C_1$-$C_4$alkyl and may contain further hetero atoms; or —$NR_{13}R_{14}$; —($C_1$-$C_4$alkylene)—$NR_{13}R_{14}$; —$N(R_{12})$—($C_1$-$C_4$alkylene)—$NR_{13}R_{14}$; —$N[(C_1$-$C_4$alkylene)—$NR_{13}R_{14}]_2$; —$N(R_{12})$—N—$R_{13}R_{14}$, wherein $R_{12}$ is hydrogen, unsubstituted or substituted $C_1$-$C_{12}$alkyl or unsubstituted or substituted aryl and $R_{13}$ and $R_{14}$, together with the nitrogen atom linking them, form an unsubstituted or substituted 5-, 6- or 7-membered ring which may contain further hetero atoms, wherein at least one nitrogen atom not bonded to one of three rings A, B and/or C is quaternised.

A likewise important use according to the invention of at least one metal complex compound of formula (1') as a catalyst for oxidation reactions is the use of such a compound wherein at least one of the substituents $R_1$ to $R_{10}$ in L' of formula (2'), preferably $R_3$, $R_5$ and/or $R_7$, is a radical

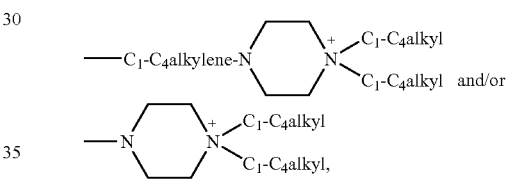

wherein the unbranched or branched alkylene group may be unsubstituted or substituted and wherein the alkyl groups, which are unbranched or branched independently of one another, may be unsubstituted or substituted.

The piperazine ring may also be unsubstituted or substituted.

A likewise especially important use according to the invention of at least one metal complex compound of formula (1') as a catalyst for oxidation reactions is the use of such a compound wherein at least one of the substituents $R_1$ to $R_{10}$ in L' of formula (2'), preferably $R_3$, $R_5$ and/or $R_7$, is a radical

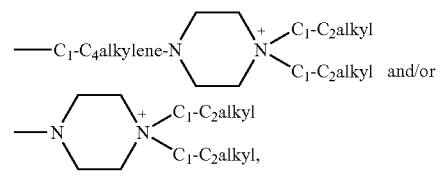

wherein the unbranched or branched alkylene group may be unsubstituted or substituted and wherein the alkyl groups, each independently of the other, may be unsubstituted or substituted.

The piperazine ring may also be unsubstituted or substituted.

Ligands L' to which preference is given are those of formula (3'a) and/or (3'b)

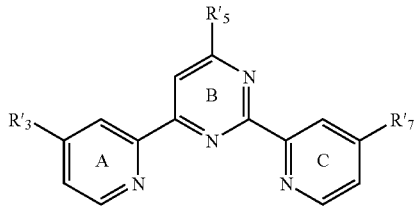
(3'a)

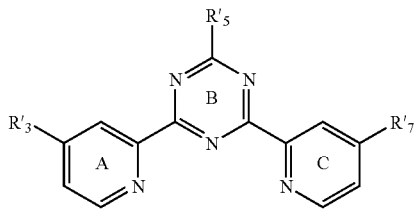
(3'b)

wherein R'$_3$, R'$_5$ and R'$_7$ have the definitions and preferred meanings indicated above for R$_5$, but R'$_3$ and R'$_7$ may additionally be hydrogen.

Ligands L' to which greater preference is given are those of formula (3'a) and/or (3'b) wherein R'$_3$, R'$_5$ and R'$_7$ have the definitions and preferred meanings indicated above for R$_5$, but R'$_3$ and R'$_7$ may additionally be hydrogen, with the proviso that (i) at least one of the substituents R'$_3$, R'$_5$ and R'$_7$ is a radical —(C$_1$-C$_6$alkylene)—N$^⊕$R$_{13}$R$_{14}$R$_{15}$; —N(R$_{12}$)—(C$_1$-C$_6$alkylene)—N$^⊕$R$_{13}$R$_{14}$R$_{15}$; —N[(C$_1$-C$_6$alkylene)—N$^⊕$R$_{13}$R$_{14}$R$_{15}$]$_2$; —N(R$_{12}$)—N$^⊕$R$_{13}$R$_{14}$R$_{15}$, wherein R$_{12}$ is as defined above and R$_{13}$, R$_{14}$ and R$_{15}$ are each independently of the others hydrogen or unsubstituted or substituted C$_1$-C$_{18}$alkyl or unsubstituted or substituted aryl, or R$_{13}$ and R$_{14}$, together with the nitrogen atom linking them, form an unsubstituted or substituted 5-, 6- or 7-membered ring which may contain further hetero atoms; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; —N(R$_{12}$)—N—R$_{13}$R$_{14}$, wherein R$_{12}$ is defined above and R$_{13}$ and R$_{14}$, together with the nitrogen atom linking them, form a 5-, 6- or 7-membered ring which may be unsubstituted or substituted by at least one unsubstituted C$_1$-C$_4$alkyl and/or substituted C$_1$-C$_4$alkyl and may contain further hetero atoms, wherein at least one nitrogen atom not bonded to one of three rings A, B and/or C is quaternised.

Ligands L' to which even greater preference is given are those of formula (3'a) and/or (3'b) wherein R'$_3$, R'$_5$ and R'$_7$ have the definitions and preferred meanings indicated above for R$_5$ but R'$_3$ and R'$_7$ may additionally be hydrogen, with the proviso that (i) at least one of the substituents R'$_3$, R'$_5$ and R'$_7$ is one of the radicals

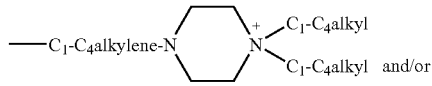

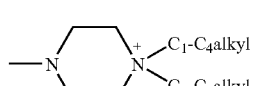

wherein the unbranched or branched alkylene group may be unsubstituted or substituted, and wherein the alkyl groups, which are branched or unbranched independently of one another, may be unsubstituted or substituted and wherein the piperazine ring may be unsubstituted or substituted.

Ligands L' to which special preference is given are those of formula (3'a) and/or (3'b) wherein R'$_3$, R'$_5$ and R'$_7$ have the definitions and preferred meanings given above for R$_5$, but R'$_3$ and R'$_7$ may additionally be hydrogen, with the proviso that (i) at least one of the substituents R'$_3$, R'$_5$ and R'$_7$ is one of the radicals

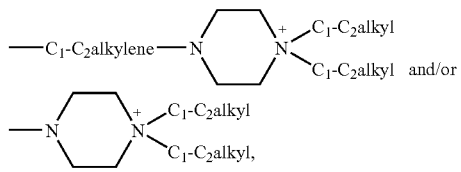

wherein the unbranched or branched alkylene group may be unsubstituted or substituted, and wherein the alkyl groups, which are branched or unbranched independently of one another, may be unsubstituted or substituted and wherein the piperazine ring may be unsubstituted or substituted.

Preferred as L' are compounds of formulae (2'), (3'a) and (3'b) in which 1 quaternised nitrogen atom is present.

Also preferred as L' are compounds of formulae (2'), (3'a) and (3'b) in which 2 or 3 quaternised nitrogen atoms are present.

Especially preferred as L' are compounds of formulae (2'), (3'a) and (3'b) in which none of the quaternised nitrogen atoms is bonded directly to one of three rings A, B and/or C.

The metal complex compounds of formulae (1) and (1') can be obtained analogously to known processes. They are obtained in a manner known per se by reacting at least one ligand L and/or L' in the desired molar ratio with a metal compound, especially a metal salt, such as the chloride, to form the corresponding metal complex. The reaction is carried out, for example, in a solvent, such as water or a lower alcohol, such as ethanol, at a temperature of, for example, from 10 to 60° C., especially at room temperature.

Ligands L and L' that are substituted by hydroxy can also be depicted in one or more tautomeric forms in accordance with the following scheme:

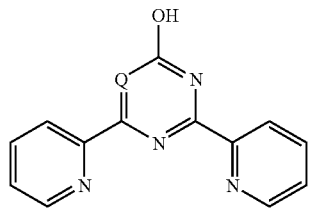 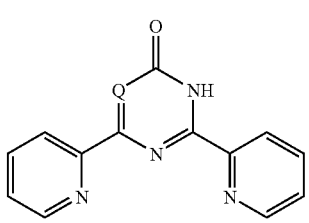

Compounds of the bispyridyl-pyrimidine type can also be prepared in a manner known per se [F. H. Case et al., J. Org. Chem. 1967, 32(5), 1591-1596]). For that purpose, for example, one part pyridine-2-carboxylate and one part ethyl acetate can be reacted with sodium hydride, and the intermediate obtained after aqueous working-up, a β-keto ester, reacted with 2-amidinopyridine, yielding the corresponding pyrimidine derivative which can be converted into the chlorine compounds by reaction with a chlorinating agent, such as, for example, $PCl_5/POCl_3$. Reaction of those compounds with amines, as desired in the presence of an excess of redox-active salts of transition metals, such as manganese, iron or ruthenium, in order to accelerate substitution, yields amine-substituted bispyridyl-pyrimidines. Preparation procedures using the latter two metal ions are described, for example, in J. Chem. Soc., Dalton Trans. 1990, 1405-1409 (E. C. Constable et al.) and New. J. Chem. 1992, 16, 855-867.

It has now been found that, in order to accelerate replacement of halide by amine on the bispyridyl-pyrimidine structure, it is also possible to use catalytic amounts of non-transition metal salts, such as, for example, zinc(II) salts, which substantially simplifies the reaction procedure and working-up.

Compounds of the bispyridyl-triazine type can be prepared analogously to known processes (e.g. Patent Applications EP 555 180 and EP 556 156 or F. H. Case et al., J. Am. Chem. Soc. 1959, 81, 905-906), by reacting two parts 2-cyanopyridine with urea or guanidine and a base.

The present invention relates also to novel metal complex compounds of formula (1a)

$$[L_nMe_mX_p]^zY_q \quad (1a)$$

wherein
Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q = z/(charge of Y), and
L is a ligand of formula (2a)

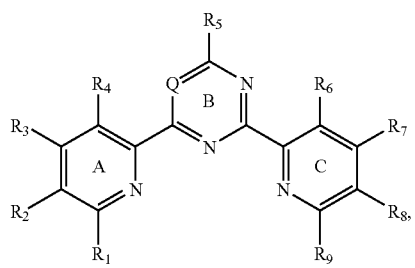

(2a)

wherein
Q is N or $CR_{10}$,
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$ wherein
$R_{11}$ is in each case hydrogen, a cation or unsubstituted or substituted $C_1$-$C_{18}$alkyl or unsubstituted or substituted aryl; —$SR_{12}$, —$SO_2R_{12}$ or —$OR_{12}$ wherein
$R_{12}$ is in each case hydrogen or unsubstituted or substituted $C_1$-$C_{18}$alkyl or unsubstituted or substituted aryl; —$NR_{13}R_{14}$; —$(C_1$-$C_6$alkylene)—$NR_{13}R_{14}$; —$N^{\oplus}R_{13}R_{14}R_{15}$; —$(C_1$-$C_6$alkylene)—$^{\oplus}R_{13}R_{14}R_{15}$; —$N(R_{12})$—$(C_1$-$C_6$alkylene)—$NR_{13}R_{14}$; —$N[(C_1$-$C_6$alkylene)—$NR_{13}R_{14}]_2$; —$N(R_{12})$—$(C_1$-$C_6$alkylene)—$N^{\oplus}R_{13}R_{14}R_{15}$; —$N[(C_1$-$C_6$alkylene)—$N^{61}R_{13}R_{14}R_{15}]_2$; —$N(R_{12})$—$N$—$R_{13}R_{14}$ or —$N(R_{12})$—$N^{\oplus}R_{13}R_{14}R_{15}$, wherein
$R_{12}$ is as defined above and
$R_{13}$, $R_{14}$ and $R_{15}$ are each independently of the other(s) hydrogen or unsubstituted or substituted $C_1$-$C_{18}$alkyl or unsubstituted or substituted aryl, or
$R_{13}$ and $R_{14}$, together with the nitrogen atom linking them, form an unsubstituted or substituted 5-, 6- or 7-membered ring which may contain further hetero atoms, Suitable substituents for the alkyl groups, aryl groups, alkylene groups or 5-, 6- or 7-membered rings are especially $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino; phenyl; phenoxy and naphthyloxy.

The $C_1$-$C_{18}$alkyl radicals mentioned for the compounds of formula (2a) are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formula (2a) are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1$-$C_4$alkyl, $C_1$-$C_4$alkoxy, phenyl and hydroxy. Special preference is given to the corresponding phenyl radicals.

The $C_1$-$C_6$alkylene groups mentioned for the compounds of formula (2a) are, for example, straight-chain or branched alkylene radicals, such as methylene, ethylene, n-propylene or n-butylene. $C_1$-$C_4$Alkylene groups are preferred. The alkylene radicals mentioned may be unsubstituted or substituted, for example by hydroxy or $C_1$-$C_4$alkoxy.

In the compounds of formulae (1a) and (2a), halogen is preferably chlorine, bromine or fluorine, with special preference being given to chlorine.

Examples of cations that come into consideration for compounds of formulae (1a) and (2a) include alkali metal cations, such as lithium, potassium and especially sodium, alkaline earth metal cations, such as magnesium and calcium, and ammonium cations. The corresponding alkali metal cations, especially sodium, are preferred.

Suitable metal ions for Me for the compounds of formula (1a) are, for example, manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt II-III, nickel II-III and copper II-III, especially iron II-IV.

For the radical X for the compounds of formula (1a) there come into consideration, for example, $CH_3CN$, $H_2O$, $F^{3-}$, $Cl^-$, $Br^-$, $HOO^-$, $O_2^{2-}$, $O^{2-}$, $R_{16}COO^-$, $R_{16}O^-$, $LMeO^-$ and $LMeOO^-$, wherein $R_{16}$ is hydrogen, —$SO_3C_1$-$C_4$alkyl or unsubstituted or substituted $C_1$-$C_{18}$alkyl or unsubstituted or substituted aryl, and $C_1$-$C_{18}$alkyl, aryl, L and Me have the definitions and preferred meanings given hereinabove and hereinbelow. Especially preferably, $R_{16}$ is hydrogen; $C_1$-$C_4$alkyl; sulfophenyl or phenyl, especially hydrogen.

As counter-ion Y for the compounds of formula (1a) there come into consideration, for example, $R_{17}COO^-$, $ClO_4^-$, $BF_4^-$, $PF_6^-$, $R_{17}SO_3^-$, $R_{17}SO_4^-$, $SO_4^{2-}$, $NO_3^-$, $F^{3-}$, $Cl^-$, $Br^-$ and $I^-$, wherein $R_{17}$ is hydrogen or unsubstituted or substituted $C_1$-$C_{18}$alkyl or unsubstituted or substituted aryl. $R_{17}$ as $C_1$-$C_{18}$alkyl or aryl has the definitions and preferred meanings given hereinabove and hereinbelow. Especially preferably, $R_{17}$ is hydrogen; $C_1$-$C_4$alkyl; phenyl or sulfophenyl, especially hydrogen or 4-sulfophenyl. The charge of the counter-ion Y is accordingly preferably 1- or 2-, especially 1-.

Y can also be a customary organic counter-ion, for example citrate, oxalate or tartrate.

For the compounds of formula (1a), n is preferably an integer having a value of from 1 to 4, preferably 1 or 2 and especially 1.

For the compounds of formula (1a), m is preferably an integer having a value of 1 or 2, especially 1.

For the compounds of formula (1a), p is preferably an integer having a value of from 0 to 4, especially 2.

For the compounds of formula (1a), z is preferably an integer having a value of from 8- to 8+, especially from 4- to 4+ and especially preferably from 0 to 4+. z is more especially the number 0.

For the compounds of formula (1a), q is preferably an integer from 0 to 8, especially from 0 to 4, and is especially preferably the number 0.

$R_{11}$ in compounds of formula (2a) is preferably hydrogen, a cation, $C_1$-$C_{12}$alkyl, unsubstituted phenyl or phenyl substituted as indicated above. Especially preferably $R_{11}$ is hydrogen, an alkali metal cation, alkaline earth metal cation or ammonium cation, $C_1$-$C_4$alkyl or phenyl, especially hydrogen or an alkali metal cation, alkaline earth metal cation or ammonium cation.

$R_{12}$ in compounds of formula (2a) is preferably hydrogen, $C_1$-$C_{12}$alkyl, unsubstituted phenyl or phenyl substituted as indicated above. Especially preferably, $R_{12}$ is hydrogen, $C_1$-$C_4$alkyl or phenyl, especially hydrogen or $C_1$-$C_4$alkyl, preferably hydrogen. Examples of the radical of formula —$OR_{12}$ that may be mentioned are hydroxy and $C_1$-$C_4$alkoxy, such as methoxy and especially ethoxy.

When $R_{13}$ and $R_{14}$ in compounds of formula (2a), together with the nitrogen atom linking them, form a 5-, 6- or 7-membered ring, that ring is preferably an unsubstituted or $C_1$-$C_4$alkyl-substituted pyrrolidine, piperidine, piperazine, morpholine or azepane ring, wherein the amino groups may be quaternised, in which case preferably the nitrogen atoms that are not bonded directly to one of the three rings A, B or C are quaternised.

The piperazine ring may, for example, be substituted by one or two unsubstituted $C_1$-$C_4$alkyl and/or substituted $C_1$-$C_4$alkyl at the nitrogen atom not bonded to the pyridine ring. In addition, $R_{13}$, $R_{14}$ and $R_{15}$ are preferably hydrogen, unsubstituted or hydroxy-substituted $C_1$-$C_{12}$alkyl, unsubstituted phenyl or phenyl substituted as indicated above. Special preference is given to hydrogen, unsubstituted or hydroxy-substituted $C_1$-$C_4$alkyl, or unsubstituted or hydroxy-substituted phenyl, especially hydrogen or unsubstituted or hydroxy-substituted $C_1$-$C_4$alkyl, preferably hydrogen.

Preference is given to ligands L of formula (2a) wherein $R_5$ is not hydrogen. $R_5$ in L of formula (2a) is preferably $C_1$-$C_{12}$alkyl; phenyl unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthyloxy; cyano; halogen; nitro; —$COOR_{11}$ or —$SO_3R_{11}$ wherein $R_{11}$ is in each case hydrogen, a cation, $C_1$-$C_{12}$alkyl, unsubstituted phenyl or phenyl substituted as indicated above; —$SR_{12}$, —$SO_2R_{12}$ or —$OR_{12}$ wherein $R_{12}$ is in each case hydrogen, $C_1$-$C_{12}$alkyl, unsubstituted phenyl or phenyl substituted as indicated above; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N(R_{12})$—($C_1$-$C_6$alkylene)—$N^{\oplus}R_{13}R_{14}R_{15}$; —$N(R_{12})$—N—$R_{13}R_{14}$ or —($R_{12}$)—$N^{\oplus}R_{13}R_{14}R_{15}$, wherein $R_{12}$ may have one of the meanings given above and $R_{13}$, $R_{14}$ and $R_{15}$ are each independently of the other(s) hydrogen, unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring unsubstituted or substituted by at least one unsubstituted $C_1$-$C_4$alkyl and/or substituted $C_1$-$C_4$alkyl, wherein the nitrogen atom may be quaternised.

$R_5$ in L of formula (2a) is especially preferably phenyl unsubstituted or substituted by $C_1$-$C_4$alkyl, $C_1$-$C_4$alkoxy, halogen, phenyl or by hydroxy; cyano; nitro; —$COOR_{11}$ or —$SO_3R_{11}$ wherein $R_{11}$ is in each case hydrogen, a cation, $C_1$-$C_4$alkyl or phenyl; —$SR_{12}$, —$SO_2R_{12}$ or —$OR_{12}$ wherein $R_{12}$ is in each case hydrogen, $C_1$-$C_4$alkyl or phenyl; —N(CH$_3$)—NH$_2$ or —NH—NH$_2$; amino; N-mono- or N,N-di-$C_1$-$C_4$alkylamino unsubstituted or substituted by hydroxy in the alkyl moiety; or an unsubstituted or $C_1$-$C_4$alkyl-substituted pyrrolidine, piperidine, piperazine, morpholine or azepane ring.

$R_5$ in L of formula (2a) is very especially preferably $C_1$-$C_4$alkoxy; hydroxy; phenyl unsubstituted or substituted by $C_1$-$C_4$alkyl, $C_1$-$C_4$alkoxy, phenyl or by hydroxy; hydrazine; amino; N-mono- or N,N-di-$C_1$-$C_4$alkylamino unsubstituted or substituted by hydroxy in the alkyl moiety; or an unsubstituted or $C_1$-$C_4$alkyl-substituted pyrrolidine, piperidine, piperazine, morpholine or azepane ring.

As radicals $R_5$ in L of formula (2a) there are especially important $C_1$-$C_4$alkoxy; hydroxy; hydrazine; amino; N-mono- or N,N-di-$C_1$-$C_4$alkylamino unsubstituted or substituted by hydroxy in the alkyl moiety; or an unsubstituted or $C_1$-$C_4$alkyl-substituted pyrrolidine, piperidine, piperazine, morpholine or azepane ring.

As radicals $R_5$ in L of formula (2a) there are very especially important $C_1$-$C_4$alkoxy; hydroxy; N-mono- or N,N-di-$C_1$-$C_4$alkylamino unsubstituted or substituted by hydroxy in the alkyl moiety; and an unsubstituted or $C_1$-$C_4$alkyl-substituted pyrrolidine, piperidine, piperazine, morpholine or azepane ring. Of those, hydroxy is of special interest.

The preferred meanings given above for $R_5$ apply also to $R_1$, $R_2$, $R_3$, $R_4$, $R_6$, $R_7$, $R_8$, $R_9$ and $R_{10}$ in L of formula (2a), but those radicals may additionally be hydrogen.

According to one embodiment of the present invention, $R_1$, $R_2$, $R_3$, $R_4$, $R_6$, $R_7$, $R_8$, $R_9$ and $R_{10}$ in L of formula (2a) are hydrogen and $R_5$ in L of formula (2a) is a radical other than hydrogen having the definition and preferred meanings indicated above.

According to a further embodiment of the present invention, $R_1$, $R_2$, $R_4$, $R_6$, $R_8$, $R_9$ and $R_{10}$ in L of formula (2a) are hydrogen and $R_3$, $R_5$ and $R_7$ in L of formula (2a) are radicals other than hydrogen, for each of which the definition and preferred meanings indicated above for $R_5$ apply.

Ligands L to which preference is given are those of formula (3a) and/or (3b)

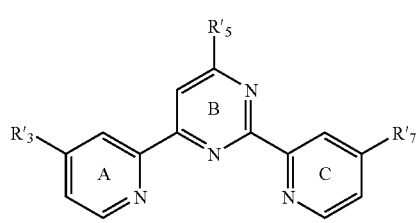

(3a)

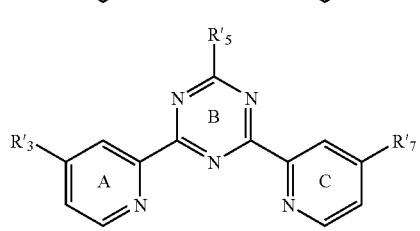

(3b)

wherein $R'_3$ and $R'_5$ have the definitions and preferred meanings indicated above for $R_3$ and $R_5$, and $R'_7$ has the definition and preferred meanings indicated above for $R_5$.

Metal complexes to which greater preference is given, especially manganese(II) and/or iron(II) complexes, of formula (1a), contain as ligands L those of formula (3a) and/or (3b)

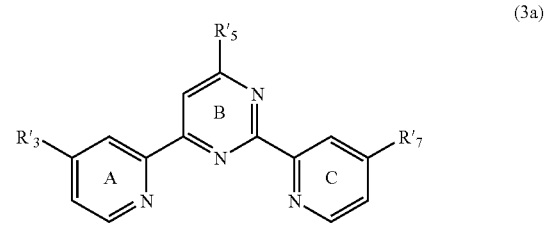

(3a)

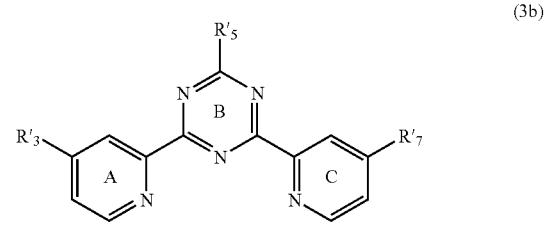

(3b)

wherein $R'_3$, $R'_5$ and $R'_7$ have the definitions and preferred meanings indicated above for $R_5$, but $R'_3$ and $R'_7$ may additionally be hydrogen.

Especially preferred metal complexes, especially manganese(II) and/or iron (II) complexes, of formula (1a), contain as ligands L those of formula (3a) and/or (3b)

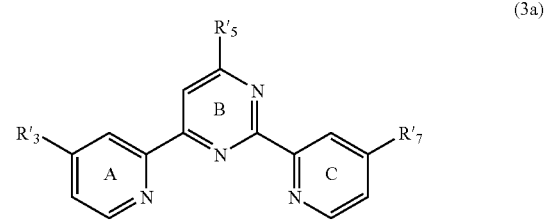

(3a)

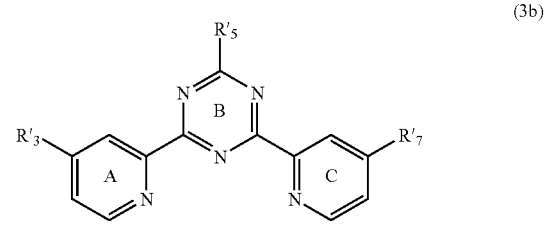

(3b)

wherein
$R'_5$ is $C_1$-$C_4$alkoxy; hydroxy; N-mono- or N,N-di-$C_1$-$C_4$alkylamino unsubstituted or substituted by hydroxy in the alkyl moiety; or —$NR_{13}R_{14}$; —($C_1$-$C_6$alkylene)—$NR_{13}R_{14}$; —$N(R_{12})$—($C_1$-$C_6$alkylene)—$NR_{13}R_{14}$; —$N[(C_1$-$C_6$alkylene)—$NR_{13}R_{14}]_2$; or —$N(R_{12})$—N—$R_{13}R_{14}$, wherein
$R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, and $R_{13}$ and $R_{14}$ are each independently of the other hydrogen, unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring, and $R'_3$ and $R'_7$ are each independently of the other hydrogen; $C_1$-$C_4$alkoxy; hydroxy; N-mono- or N,N-di-$C_1$-$C_4$alkylamino substituted by hydroxy in the alkyl moiety; or —$NR_{13}R_{14}$; —($C_1$-$C_6$alkylene)—$NR_{13}R_{14}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—$N$—$R_{13}R_{14}$, wherein $R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, and $R_{13}$ and $R_{14}$ are each independently of the other hydrogen; unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring.

The present invention relates also to novel metal complex compounds of formula (1'a)

$$[L'_n Me_m X_p]^z Y_q \quad (1'a),$$

wherein
Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge of Y), and
L' is a ligand of formula (2'a)

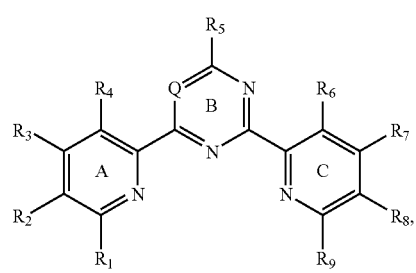

wherein
Q is N or $CR_{10}$,
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$ wherein $R_{11}$ is in each case hydrogen, a cation or unsubstituted or substituted $C_1$-$C_{18}$alkyl or unsubstituted or substituted aryl; —$SR_{12}$, —$SO_2R_{12}$ or —$OR_{12}$ wherein $R_{12}$ is in each case hydrogen or unsubstituted or substituted $C_1$-$C_{18}$alkyl or substituted or unsubstituted aryl; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—$N$—$R_{13}R_{14}$ or —$N(R_{12})$—$N^{\oplus}R_{13}R_{14}R_{15}$, wherein $R_{12}$ is as defined above and $R_{13}$, $R_{14}$ and $R_{15}$ are each independently of the other(s) hydrogen or unsubstituted or substituted $C_1$-$C_{18}$alkyl or substituted or unsubstituted aryl, or $R_{13}$ and $R_{14}$, together with the nitrogen atom linking them, form an unsubstituted or substituted 5-, 6- or 7-membered ring which may contain further hetero atoms, with the proviso that, at least one of the substituents $R_1$ to $R_{10}$ contains a quaternised nitrogen atom that is not bonded directly to one of the three rings A, B and/or C.

Suitable substituents for the alkyl groups, aryl groups, alkylene groups or 5-, 6- or 7-membered rings are especially $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino; phenyl; phenoxy or naphthyloxy.

The $C_1$-$C_{18}$alkyl radicals mentioned for the compounds of formula (2'a) are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formula (2'a) are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1$-$C_4$alkyl, $C_1$-$C_4$alkoxy, phenyl and hydroxy. Special preference is given to the corresponding phenyl radicals.

The $C_1$-$C_6$alkylene groups mentioned for the compounds of formula (2'a) are, for example, straight-chain or branched alkylene radicals, such as methylene, ethylene, n-propylene or n-butylene. $C_1$-$C_4$Alkylene groups are preferred. The alkylene radicals mentioned may be unsubstituted or substituted, for example by hydroxy or $C_1$-$C_4$alkoxy.

In the compounds of formulae (1'a) and (2'a), halogen is preferably chlorine, bromine or fluorine, with special preference being given to chlorine.

Examples of cations that come into consideration for compounds of formulae (1'a) and (2'a) include alkali metal cations, such as lithium, potassium and especially sodium, alkaline earth metal cations, such as magnesium and calcium, and ammonium cations. The alkali metal cations, especially sodium, are preferred.

Suitable metal ions for Me for the compounds of formula (1'a) are, for example, manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt II-III, nickel II-III and copper II-III, especially iron II-IV.

For the radical X for the compounds of formula (1'a) there come into consideration, for example, $CH_3CN$, $H_2O$, $F^-$, $Cl^-$, $Br^-$, $HOO^-$, $O_2^{2-}$, $O^{2-}$, $R_{16}COO^-$, $R_{16}O^-$, $LMeO^-$ and $LMeOO^-$, wherein $R_{16}$ is hydrogen, $-SO_3C_1$-$C_4$alkyl or unsubstituted or substituted $C_1$-$C_{18}$alkyl or substituted or unsubstituted aryl, and $C_1$-$C_{18}$alkyl, aryl, L and Me have the definitions and preferred meanings given hereinabove and hereinbelow. Especially preferably, $R_{16}$ is hydrogen; $C_1$-$C_4$alkyl; sulfophenyl or phenyl, especially hydrogen.

As counter-ion Y for the compounds of formula (1'a) there come into consideration, for example, $R_{17}COO^-$, $ClO_4^-$, $BF_4^-$, $PF_6^-$, $R_{17}SO_3^-$, $R_{17}SO_4^-$, $SO_4^{2-}$, $NO_3^-$, $F^-$, $Cl^-$, $Br^-$ and $I^-$, wherein $R_{17}$ is hydrogen or unsubstituted or substituted $C_1$-$C_{18}$alkyl or substituted or unsubstituted aryl. $R_{17}$ as $C_1$-$C_{18}$alkyl or aryl has the definitions and preferred meanings given hereinabove and hereinbelow. Especially preferably, $R_{17}$ is hydrogen; $C_1$-$C_4$alkyl; phenyl or sulfophenyl, especially hydrogen or 4-sulfophenyl. The charge of the counter-ion Y is accordingly preferably 1- or 2-, especially 1-.

Y can also be a customary organic counter-ion, for example citrate, oxalate or tartrate.

For the compounds of formula (1'a), n is preferably an integer having a value of from 1 to 4, preferably 1 or 2 and especially 1.

For the compounds of formula (1'a), m is preferably an integer having a value of 1 or 2, especially 1.

For the compounds of formula (1'a), p is preferably an integer having a value of from 0 to 4, especially 2.

For the compounds of formula (1'a), z is preferably an integer having a value of from 8– to 8+, especially from 4– to 4+ and especially preferably from 0 to 4+. z is more especially the number 0.

For the compounds of formula (1'a), q is preferably an integer from 0 to 8, especially from 0 to 4, and is especially preferably the number 0.

$R_{11}$ in compounds of formula (2'a) is preferably hydrogen, a cation, $C_1$-$C_{12}$alkyl, unsubstituted phenyl or phenyl substituted as indicated above. Especially preferably, $R_{11}$ is hydrogen, an alkali metal cation, alkaline earth metal cation or ammonium cation, $C_1$-$C_4$alkyl or phenyl, especially hydrogen or an alkali metal cation, alkaline earth metal cation or ammonium cation.

$R_{12}$ in compounds of formula (2'a) is preferably hydrogen, $C_1$-$C_{12}$alkyl, unsubstituted phenyl or phenyl substituted as indicated above. Especially preferably, $R_{12}$ is hydrogen, $C_1$-$C_4$alkyl or phenyl, especially hydrogen or $C_1$-$C_4$alkyl, preferably hydrogen. Examples of the radical of formula $-OR_{12}$ that may be mentioned are hydroxy and $C_1$-$C_4$alkoxy, such as methoxy and especially ethoxy.

When $R_{13}$ and $R_{14}$ in compounds of formula (2'a), together with the nitrogen atom linking them, form a 5-, 6- or 7-membered ring, that ring is preferably an unsubstituted or $C_1$-$C_4$alkyl-substituted pyrrolidine, piperidine, piperazine, morpholine or azepane ring, wherein the amino groups may be quaternised, in which case preferably the nitrogen atoms that are not bonded directly to one of the three rings A, B or C are quaternised.

The piperazine ring may, for example, be substituted by one or two unsubstituted $C_1$-$C_4$alkyl and/or substituted $C_1$-$C_4$alkyl at the nitrogen atom not bonded to the pyridine ring. In addition, $R_{13}$, $R_{14}$ and $R_{15}$ are preferably hydrogen, unsubstituted or hydroxy-substituted $C_1$-$C_{12}$alkyl, unsubstituted phenyl or phenyl substituted as indicated above. Special preference is given to hydrogen, unsubstituted or hydroxy-substituted $C_1$-$C_4$alkyl, or unsubstituted or hydroxy-substituted phenyl, especially hydrogen or unsubstituted or hydroxy-substituted $C_1$-$C_4$alkyl, preferably hydrogen.

Preference is given to ligands L' of formula (3'a) and/or (3'b)

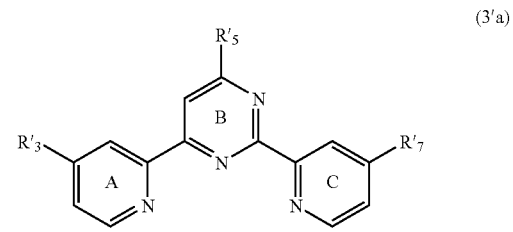

(3'a)

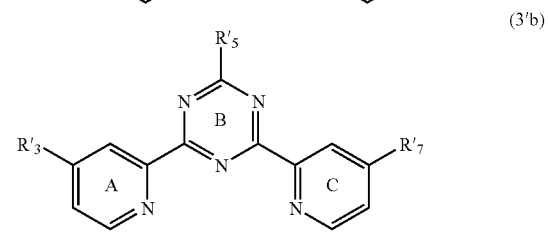

(3'b)

wherein $R'_3$, $R'_5$ and $R'_7$ have the definitions and preferred meanings indicated above for $R_5$, but $R'_3$ and $R'_7$ may additionally be hydrogen.

Ligands L' to which greater preference is given are those of formula (3'a) and/or (3'b) wherein $R'_3$, $R'_5$ and $R'_7$ have the definitions and preferred meanings indicated above for $R_5$, but $R'_3$ and $R'_7$ may additionally be hydrogen, with the proviso that (i) at least one of the substituents $R'_3$, $R'_5$ and $R'_7$ is a radical $-(C_1$-$C_6$alkylene$)-N^{\oplus}R_{13}R_{14}R_{15}$; $-N(R_{12})-(C_1$-$C_6$alkylene$)-N^{\oplus}(R_{13}R_{14}R_{15}$; $-N[(C_1$-$C_6$alkylene$)-N^{\oplus}R_{13}R_{14}R_{15}]_2$; $-N(R_{12})-N^{\oplus}R_{13}R_{14}R_{15}$, wherein $R_{12}$ is as defined above and $R_{13}$, $R_{14}$ and $R_{15}$ are each independently of the others hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms; or $-NR_{13}R_{14}$; $-(C_1$-$C_6$alkylene$)-NR_{13}R_{14}$; $-N(R_{12})-(C_{C6}$alkylene$)-NR_{13}R_{14}$; $-N[(C_1$-$C_6$alkylene$)-NR_{13}R_{14}]_2$; $-N(R_{12})-N-R_{13}R_{14}$, wherein $R_{12}$ and $R_{15}$ are as defined above and $R_{13}$ and $R_{14}$, together with the nitrogen atom linking them, form a 5-, 6- or 7-membered ring which may be unsubstituted or substituted by at least one unsubstituted $C_1$-$C_4$alkyl and/or substituted $C_1$-$C_4$alkyl and may contain further hetero atoms, wherein at least one nitrogen atom not bonded to one of the rings A, B and 7 or C is quaternised.

Ligands L' to which even greater preference is given are those of formula (3'a) and/or (3'b) wherein $R'_3$, $R'_5$ and $R'_7$ have the definitions and preferred meanings indicated above for $R_5$ but $R'_3$ and $R'_7$ may additionally be hydrogen, with the proviso that (i) at least one of the substituents $R'_3$, $R'_5$ and $R'_7$ is one of the radicals

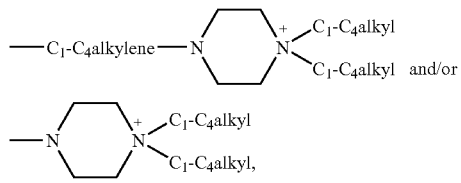

wherein the unbranched or branched alkylene group may be unsubstituted or substituted, and wherein the alkyl groups, which are branched or unbranched independently of one another, may be unsubstituted or substituted and wherein the piperazine ring may be unsubstituted or substituted.

Ligands L' to which special preference is given are those of formula (3'a) and/or (3'b) wherein $R'_3$, $R'_5$ and $R'_7$ have the definitions and preferred meanings given above for $R_5$, but $R'_3$ and $R'_7$ may additionally be hydrogen, with the proviso that (i) at least one of the substituents $R'_3$, $R'_5$ and $R'_7$ is one of the radicals

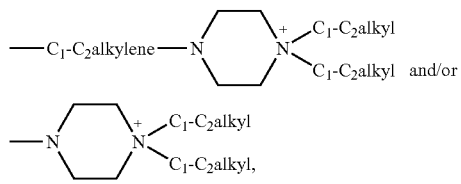

wherein the unbranched or branched alkylene group may be unsubstituted or substituted, and wherein the alkyl groups, which are branched or unbranched independently of one another, may be unsubstituted or substituted and wherein the piperazine ring may be unsubstituted or substituted.

Preferred as L' are compounds of formulae (2'), (3'a) and (3'b) in which 1 quaternised nitrogen atom is present.

Also preferred as L' are compounds of formulae (2'), (3'a) and (3'b) in which 2 or 3 quaternised nitrogen atoms are present.

Especially preferred as L' are compounds of formulae (2'), (3'a) and (3'b) in which none of the quaternised nitrogen atoms is bonded directly to one of the rings A, B or C.

The present invention relates also to the novel ligands L' of formulae (4') and (5')

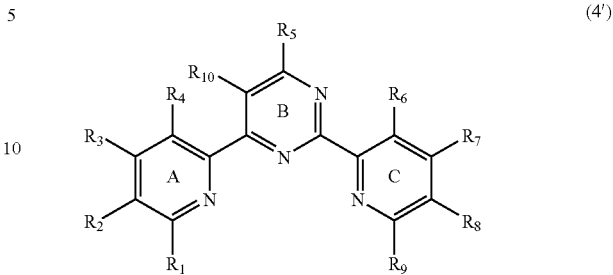

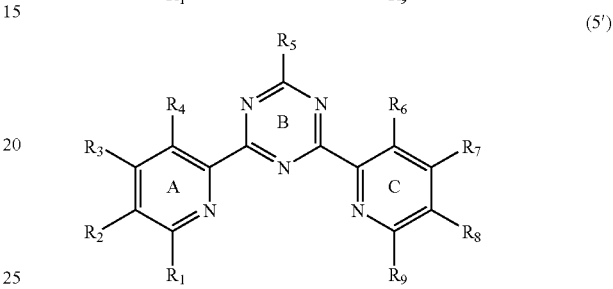

wherein
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$ wherein
$R_{11}$ is in each case hydrogen, a cation or unsubstituted or substituted $C_1$-$C_{18}$alkyl or unsubstituted or substituted aryl; —$SR_{12}$, —$SO_2R_{12}$ or —$OR_{12}$ wherein
$R_{12}$ is in each case hydrogen or unsubstituted or substituted $C_1$-$C_{18}$alkyl or unsubstituted or substituted aryl; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus 61}R_{13}R_{14}R_{15}]_2$; —$N(R_{12})$—N—$R_{13}R_{14}$ or —$N(R_{12})$—$N^{\oplus}R_{13}R_{14}R_{15}$, wherein
$R_{12}$ is as defined above and
$R_{13}$, $R_{14}$ and $R_{15}$ are each independently of the other(s) hydrogen or unsubstituted or substituted $C_1$-$C_{18}$alkyl or unsubstituted or substituted aryl, or
$R_{13}$ and $R_{14}$, together with the nitrogen atom linking them, form an unsubstituted or substituted 5-, 6- or 7-membered ring which may contain further hetero atoms, with the proviso that at least one of the substituents $R_1$ to $R_{10}$ contains a quaternised nitrogen atom that is not bonded directly to one of the three rings A, B and/or C.

Suitable substituents for the alkyl groups, aryl groups, alkylene groups or 5-, 6- or 7-membered rings are especially $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino; phenyl; phenoxy and naphthyloxy.

The $C_1$-$C_{18}$alkyl radicals mentioned for the compounds of formulae (4') and (5') are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formulae (4') and (5') are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, amino, wherein the amino groups may be quaternised, phenyl, phenoxy or by naphthyloxy. Preferred substituents are $C_1$-$C_4$alkyl, $C_1$-$C_4$alkoxy, phenyl and hydroxy. Special preference is given to the corresponding phenyl radicals.

The $C_1$-$C_6$alkylene groups mentioned for the compounds of formulae (4') and (5') are, for example, straight-chain or branched alkylene radicals, such as methylene, ethylene, n-propylene or n-butylene. $C_1$-$C_4$Alkylene groups are preferred. The alkylene radicals mentioned may be unsubstituted or substituted, for example by hydroxy or $C_1$-$C_4$alkoxy.

Examples of cations that come into consideration for compounds of formulae (4') and (5') include alkali metal cations, such as lithium, potassium and especially sodium, alkaline earth metal cations, such as magnesium and calcium, and ammonium cations. The corresponding alkali metal cations, especially sodium, are preferred.

In the compounds of formulae (4') and (5'), halogen is preferably chlorine, bromine or fluorine, with special preference being given to chlorine.

$R_{11}$ in compounds of formulae (4') and (5') is preferably hydrogen, a cation, $C_1$-$C_{12}$alkyl, unsubstituted phenyl or phenyl substituted as indicated above. Especially preferably, $R_{11}$ is hydrogen, an alkali metal cation, alkaline earth metal cation or ammonium cation, $C_1$-$C_4$alkyl or phenyl, especially hydrogen or an alkali metal cation, alkaline earth metal cation or ammonium cation.

$R_{12}$ in compounds of formulae (4') and (5') is preferably hydrogen, $C_1$-$C_{12}$alkyl, unsubstituted phenyl or phenyl substituted as indicated above. Especially preferably, $R_{12}$ is hydrogen, $C_1$-$C_4$alkyl or phenyl, especially hydrogen or $C_1$-$C_4$alkyl, preferably hydrogen. Examples of the radical of formula —$OR_{12}$ that may be mentioned are hydroxy and $C_1$-$C_4$alkoxy, such as methoxy and especially ethoxy.

When $R_{13}$ and $R_{14}$ in compounds of formulae (4') and (5'), together with the nitrogen atom linking them, form a 5-, 6- or 7-membered ring, that ring is preferably an unsubstituted or $C_1$-$C_4$alkyl-substituted pyrrolidine, piperidine, piperazine, morpholine or azepane ring, wherein the amino groups may be quaternised, in which case preferably the nitrogen atoms that are not bonded directly to one of the three rings A, B and/or C are quaternised. The piperazine ring may, for example, be substituted by one or two unsubstituted $C_1$-$C_4$alkyl and/or substituted $C_1$-$C_4$alkyl at the nitrogen atom not bonded to the pyridine ring. In addition, $R_{13}$, $R_{14}$ and $R_{15}$ are preferably hydrogen, unsubstituted or hydroxy-substituted $C_1$-$C_{12}$alkyl, unsubstituted phenyl or phenyl substituted as indicated above. Special preference is given to hydrogen, unsubstituted or hydroxy-substituted $C_1$-$C_4$alkyl, or phenyl, especially hydrogen or unsubstituted or hydroxy-substituted $C_1$-$C_4$alkyl, preferably hydrogen. Preference is given to compounds of formulae (4') and (5') wherein $R_5$ is not hydrogen.

Preference is given to compounds of formulae (4') and (5') wherein $R_5$ is preferably phenyl unsubstituted or substituted by $C_1$-$C_4$alkyl, $C_1$-$C_4$alkoxy, halogen, phenyl or by hydroxy; cyano; nitro; —$COOR_{11}$ or —$SO_3R_{11}$ wherein $R_{11}$ is in each case hydrogen, a cation, $C_1$-$C_4$alkyl or phenyl; —$SR_{12}$, —$SO_2R_{12}$ or —$OR_{12}$ wherein $R_{12}$ is in each case hydrogen, $C_1$-$C_4$alkyl or phenyl; —N($CH_3$)—$NH_2$ or —NH—$NH_2$; amino; N-mono- or N,N-di-$C_1$-$C_4$alkylamino unsubstituted or substituted by hydroxy in the alkyl moiety wherein the nitrogen atoms, especially the nitrogen atoms not bonded to one of the three rings A, B or C, may be quaternised; N-mono- or N,N-di-$C_1$-$C_4$alkyl—$N^{\oplus}R_{13}R_{14}R_{15}$ unsubstituted or substituted by hydroxy in the alkyl moiety, wherein $R_{13}$, $R_{14}$ and $R_{15}$ are each independently of the others hydrogen, unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring unsubstituted or substituted by at least one $C_1$-$C_4$alkyl or by at least one unsubstituted $C_1$-$C_4$alkyl and/or substituted $C_1$-$C_4$alkyl, wherein the nitrogen atom may be quaternised; or N-mono- or N,N-di-$C_1$-$C_4$alkyl-$NR_{13}R_{14}$ unsubstituted or substituted by hydroxy in the alkyl moiety, wherein $R_{13}$ and $R_{14}$ may be as defined above.

$R_5$ in compounds of formulae (4') and (5') is very especially $C_1$-$C_4$alkoxy; hydroxy; phenyl unsubstituted or substituted by $C_1$-$C_4$alkyl, $C_1$-$C_4$alkoxy, phenyl or by hydroxy; hydrazine; amino; N-mono- or N,N-di-$C_1$-$C_4$alkylamino unsubstituted or substituted by hydroxy in the alkyl moiety, wherein the nitrogen atoms, especially the nitrogen atoms not bonded to one of the three rings A, B or C, may be quaternised; or a pyrrolidine, piperidine, morpholine or alzepane ring unsubstituted or substituted by one or two unsubstituted $C_1$-$C_4$alkyl and/or substituted $C_1$-$C_4$alkyl, wherein the nitrogen atom may be quaternised.

A likewise very especially preferred radical that may be mentioned for $R_5$ in compounds of formulae (4') and (5') is

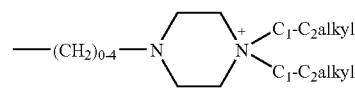

wherein the ring, the alkylene group and the two alkyl groups may additionally be substituted.

As radicals $R_5$ in compounds of formulae (4') and (5') there are especially important $C_1$-$C_4$alkoxy; hydroxy; hydrazine; amino; N-mono- or N,N-di-$C_1$-$C_4$alkylamino unsubstituted or substituted by hydroxy in the alkyl moiety, wherein the nitrogen atoms, especially the nitrogen atoms not bonded to one of the three rings A, B or C, may be quaternised; or a pyrrolidine, piperidine, piperazine, morpholine or azepane ring unsubstituted or substituted by at least one $C_1$-$C_4$alkyl, wherein the nitrogen atoms may be quaternised.

As a further, especially important example of $R_5$ in compounds of formulae (4') and (5') the following radical may be mentioned:

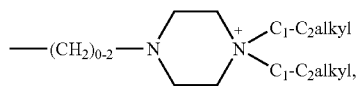

wherein the ring, the alkylene group and the two alkyl groups may additionally independently from each other substituted.

As radicals $R_5$ in compounds of formulae (4') and (5') there are especially important $C_1$-$C_4$alkoxy; hydroxy; N-mono- or N,N-di-$C_1$-$C_4$alkylamino substituted by hydroxy in the alkyl moiety, wherein the nitrogen atoms, especially the nitrogen atoms not bonded to one of the three rings A, B or C, may be quaternised; or a pyrrolidine, piperidine, morpholine or azepane ring unsubstituted or substituted by at least one $C_1$-$C_4$alkyl, wherein the amino groups may be quaternised.

As examples of the radical $R_5$ in compounds of formulae (4') and (5') mention may be made especially of —OH;

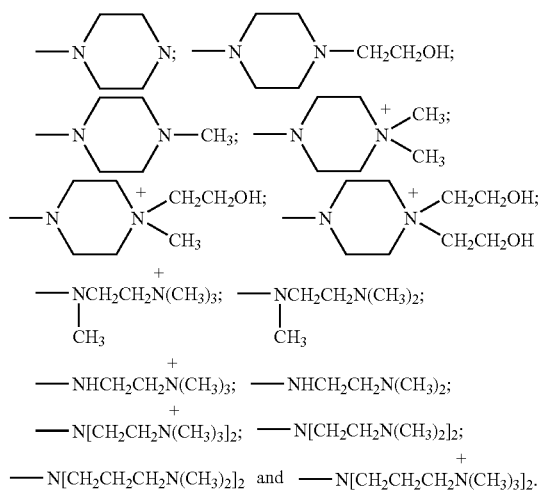

Of those, hydroxy is of special interest.

The preferred meanings given above for $R_5$ in L' of formula (2') apply also to $R_1$, $R_2$, $R_3$, $R_4$, $R_6$, $R_7$, $R_8$, $R_9$ and $R_{10}$ in compounds of formulae (4') and (5'), but those radicals may additionally be hydrogen.

According to one embodiment of the present invention, $R_1$, $R_2$, $R_3$, $R_4$, $R_6$, $R_7$, $R_8$, $R_9$ and $R_{10}$ in compounds of formulae (4') and (5') are hydrogen and $R_5$ in L' of formula (2') is a radical other than hydrogen having the definition and preferred meanings indicated above.

According to a further embodiment of the present invention, $R_1$, $R_2$, $R_4$, $R_6$, $R_8$, $R_9$ and $R_{10}$ in compounds of formulae (4') and (5') are hydrogen and $R_3$, $R_5$ and $R_7$ in compounds of formulae (4') and (5') are radicals other than hydrogen, for each of which the definitions and preferred meanings indicated above for $R_5$ apply.

Preference is likewise given to compounds of formulae (4') and (5') wherein at least one of the substituents $R_1$ to $R_{10}$, preferably $R_3$, $R_5$ and/or $R_7$, is one of the following radicals: —($C_1$-$C_6$alkylene)—$N^{\oplus}R_{13}R_{14}R_{15}$; —N($R^2$)—($C_1$-$C_6$alkylene)—$N^{61}$ $R_{13}R_{14}R_{15}$; —N[($C_1$-$C_6$alkylene)—$N^{61}$ $R_{13}R_{14}R_{15}]_2$; or —N($R_{12}$)—$N^{\oplus}R_{13}R_{14}R_{15}$, wherein $R_{12}$ is as defined above and $R_{13}$, $R_{14}$ and $R_{15}$ are each independently of the others hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms; or —$NR_{13}R_{14}$; —($C_1$-$C_6$alkylene)—$NR_{13}R_{14}$; —N($R_{12}$)—($C_1$-$C_6$alkylene)—$NR_{13}R_{14}$; —N[($C_1$-$C_6$alkylene)—$NR_{13}R_{14}]_2$; or —N($R_{12}$)—N—$R_{13}R_{14}$, wherein $R_{12}$ and $R_{15}$ are as defined above and $R_{13}$ and $R_{14}$, together with the nitrogen atom linking them, form a 5-, 6- or 7-membered ring which is unsubstituted or substituted by at least one unsubstituted $C_1$-$C_4$alkyl and/or substituted $C_1$-$C_4$alkyl and may contain further hetero atoms, wherein at least one nitrogen atom not bonded to one of the rings A, B and/or C is quaternised.

Greater preference is likewise given to compounds of formulae (4') and (5') according to the invention wherein at least one of the substituents $R_1$ to $R_{10}$, preferably $R_3$, $R_5$ and/or $R_7$, is one of the following radicals: —($C_1$-$C_4$alkylene)—$N^{\oplus}R_{13}R_{14}R_{15}$; —N($R_{12}$)—($C_1$-$C_4$alkylene)—$N^{\oplus}R_{13}R_{14}R_{15}$; —N[($C_1$-$C_4$alkylene)—$N^{\oplus}R_{13}R_{14}R_{15}]_2$; or —N($R_{12}$)—$N^{\oplus}R_{13}R_{14}R_{15}$, wherein $R_{12}$ is hydrogen, unsubstituted or substituted $C_1$-$C_{12}$alkyl or unsubstituted or substituted aryl and $R_{13}$, $R_{14}$ and $R_{15}$ are each independently of the others hydrogen or unsubstituted or substituted $C_1$-$C_{12}$alkyl or substituted or unsubstituted aryl, or $R_{13}$ and $R_{14}$, together with the nitrogen atom linking them, form a 5-, 6- or 7-membered ring which is unsubstituted or substituted by at least one unsubstituted $C_1$-$C_4$alkyl and/or substituted $C_1$-$C_4$alkyl and may contain further hetero atoms; or —$NR_{13}R_{14}$; —($C_1$-$C_4$alkylene)—$NR_{13}R_{14}$; —N($R_{12}$)—($C_1$-$C_4$alkylene)—$NR_{13}R_{14}$; —N[($C_1$-$C_4$alkylene)—$NR_{13}R_{14}]_2$; or —N($R_{12}$)—N—$R_{13}R_{14}$, wherein $R_{12}$ is hydrogen unsubstituted or substituted $C_1$-$C_{12}$alkyl or substituted or unsubstituted aryl, and $R_{13}$ and $R_{14}$, together with the nitrogen atom linking them, form an unsubstituted or substituted 5-, 6- or 7-membered ring which may contain further hetero atoms, wherein at least one nitrogen atom not bonded to one of the rings A, B and/or C is quaternised.

Also important are compounds of formulae (4') and (5') wherein at least one of the substituents $R_1$ to $R_{10}$, preferably $R_3$, $R_5$ and/or $R_7$, is a radical

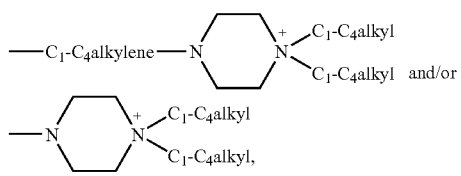

wherein the unbranched or branched alkylene group may be unsubstituted or substituted and wherein the alkyl groups, which are unbranched or branched independently of one another, may be unsubstituted or substituted.

The piperazine ring may also be unsubstituted or substituted.

Also especially important are compounds of formulae (4') and (5') wherein at least one of the substituents $R_1$ to $R_{10}$, preferably $R_3$, $R_5$ and/or $R_7$, is a radical

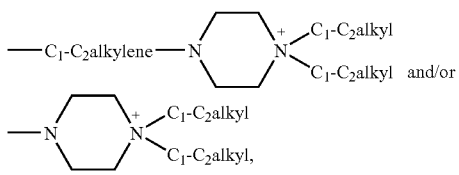

wherein the unbranched or branched alkylene group may be unsubstituted or substituted and wherein the alkyl groups, each independently of the other, may be unsubstituted or substituted.

The piperazine ring may also be unsubstituted or substituted.

Compounds of formulae (4') and (5') to which preference is given are those of formula (4'a) and/or (5'a)

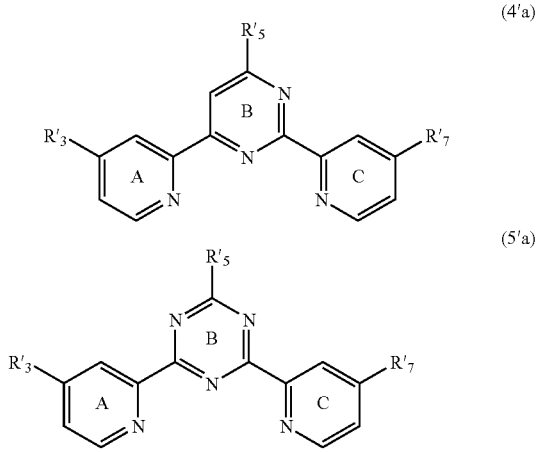

wherein $R'_3$, $R'_5$ and $R'_7$ have the definitions and preferred meanings given above for $R_5$ in compounds of formulae (4') and (5'), but $R'_3$ and $R'_7$ may additionally be hydrogen.

Greater preference is given to compounds of formulae (4'a) and (5'a) wherein $R'_3$, $R'_5$ and $R'_7$ have the definitions and preferred meanings given above for $R_5$, but $R'_3$ and $R'_7$ may additionally be hydrogen, with the proviso that
(i) at least one of the substituents $R'_3$, $R'_5$ and $R'_7$ is a radical
—($C_1$-$C_6$alkylene)—$N^{\oplus}R_{13}R_{14}R_{15}$;  —$N(R_{12})$—($C_{C6}$alkylene)—$N^{\oplus}R_{13}R_{14}R_{15}$;  —$N[(C_1$-$C_6$alkylene)—$N^{\oplus}R_{13}R_{14}R_{15}]_2$; or —$N(R_{12})$—$N^{\oplus}R_{13}R_{14}R_{15}$, wherein $R_{12}$ is as defined above and $R_{13}$, $R_{14}$ and $R_{15}$ are each independently of the others hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms; or —$NR_{13}R_{14}$; —($C_1$-$C_6$alkylene)—$NR_{13}R_{14}$; —$N(R_{12})$—($C_1$-$C_6$alkylene)—$NR_{13}R_{14}$; —$N[(C_1$-$C_6$alkylene)—$NR_{13}R_{14}]_2$; or —$N(R_{12})$—$N$—$R_{13}R_{14}$, wherein $R_{12}$ is as defined above and $R_{13}$ and $R_{14}$, together with the nitrogen atom linking them, form a 5-, 6- or 7-membered ring which may be unsubstituted or substituted by at least one unsubstituted $C_1$-$C_4$alkyl and/or substituted $C_1$-$C_4$alkyl and may contain further hetero atoms, wherein at least one nitrogen atom not bonded to one of the rings A, B and/or C is quaternised.

Even greater preference is given to compounds of formulae (4'a) and (5'a) wherein $R'_3$, $R'_5$ and $R'_7$ have the definitions and preferred meanings given above for $R_5$, but $R'_3$ and $R'_7$ may additionally be hydrogen, with the proviso that
(i) at least one of the substituents $R'_3$, $R'_5$ and $R'_7$ is one of the radicals

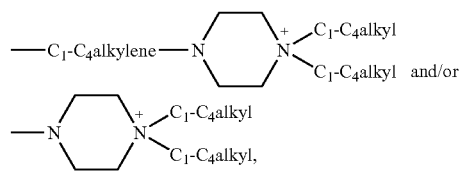

wherein the unbranched or branched alkylene group may be unsubstituted or substituted, and wherein the alkyl groups, which are branched or unbranched independently of one another, may be unsubstituted or substituted and wherein the piperazine ring may be unsubstituted or substituted.

Special preference is given to compounds of formulae (4'a) and (5'a) wherein $R'_3$, $R'_5$ and $R'_7$ have the definitions and preferred meanings given above for $R_5$, but $R'_3$ and $R'_7$ may additionally be hydrogen, with the proviso that
(i) at least one of the substituents $R'_3$, $R'_5$ and $R'_7$ is one of the radicals

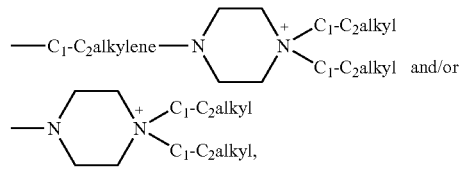

wherein the unbranched or branched alkylene group may be unsubstituted or substituted, and wherein the alkyl groups, which are branched or unbranched independently of one another, may be unsubstituted or substituted and wherein the piperazine ring may be unsubstituted or substituted.

Preference is given to compounds of formulae (4'), (4'a), (5') and (5'a) in which 1 quaternised nitrogen atom is present.

Preference is likewise given to compounds of formulae (4'), (4'a), (5') and (5'a) in which 2 or 3 quaternised nitrogen atoms are present.

Special preference is given to compounds of formulae (4'), (4'a), (5') and (5'a) in which none of the quaternised nitrogen atoms is bonded directly to one of the rings A, B and/or C.

The present invention relates also to novel ligands L of formula (6)

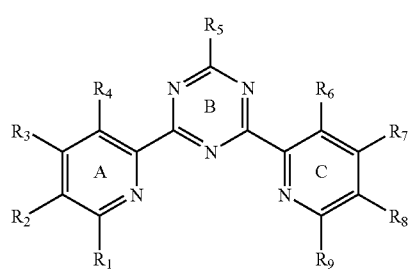

wherein $R_1$, $R_2$, $R_4$, $R_5$, $R_6$, $R_7$, $R_8$ and $R_9$ are each independently of the others hydrogen; unsubstituted or substituted $C_1$-$C_{18}$alkyl or unsubstituted or substituted aryl; cyano; halogen; nitro; —COOR$_{11}$ or —SO$_3$R$_{11}$ wherein $R_{11}$ is in each case hydrogen, a cation or unsubstituted or substituted $C_1$-$C_{18}$alkyl or unsubstituted or substituted aryl; —SR$_{12}$, —SO$_2$R$_{12}$ or —OR$_{12}$ wherein $R_{12}$ is in each case hydrogen or unsubstituted or substituted $C_1$-$C_{18}$alkyl or unsubstituted or substituted aryl; —NR$_{13}$R$_{14}$; —(C$_1$-C$_6$alkylene)—NR$_{13}$R$_{14}$; —N$^\oplus$R$_{13}$R$_{14}$R$_{15}$; —(C$_1$-C$_6$alkylene)—N$^\oplus$R$_{13}$R$_{14}$R$_{15}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; —N(R$_{12}$)—(C$_1$-C$_6$alkylene)—N$^\oplus$R$_{13}$R$_{14}$R$_{15}$; —N[(C$_1$-C$_6$alkylene)—N$^\oplus$R$_{13}$R$_{14}$R$_{15}$]$_2$; —N(R$_{12}$)—N—R$_{13}$R$_{14}$; or —N(R$_{12}$)—N$^\oplus$R$_{13}$R$_{14}$R$_{15}$, wherein $R_{12}$ is as defined above and $R_{13}$, $R_{14}$ and $R_{15}$ are each independently of the other(s) hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms, and $R_3$ is phenyl substituted by $C_1$-$C_4$alkyl, $C_1$-$C_4$alkoxy, hydroxy, sulfo, sulfato, halogen, cyano, nitro, carboxy, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthyloxy, substituted $C_1$-$C_{18}$alkyl or substituted or unsubstituted aryl; —CH$_3$; $C_3$-$C_{18}$alkyl; cyano; halogen; nitro; —COOR$_{11}$ or —SO$_3$R$_{11}$ wherein $R_{11}$ is in each case hydrogen, a cation or substituted $C_1$-$C_{18}$alkyl or unsubstituted or substituted aryl; —SR$_{12}$, —SO$_2$R$_{12}$ or —OR$_{12}$ wherein $R_{12}$ is in each case hydrogen or unsubstituted or substituted $C_1$-$C_{18}$alkyl or unsubstituted or substituted aryl; —NR$_{13}$R$_{14}$; —(C$_1$-C$_6$alkylene)—NR$_{13}$R$_{14}$; —N$^\oplus$R$_{13}$R$_{14}$R$_{15}$; —(C$_1$-C$_6$alkylene)—N$^\oplus$R$_{13}$R$_{14}$R$_{15}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; —N(R$_{12}$)—(C$_1$-C$_6$alkylene)—N$^\oplus$R$_{13}$R$_{14}$R$_{15}$; —N[(C$_1$-C$_6$alkylene)—N$^\oplus$R$_{13}$R$_{14}$R$_{15}$]$_2$; —N(R$_{12}$)—N—R$_{13}$R$_{14}$; or —N(R$_{12}$)—N$^\oplus$R$_{13}$R$_{14}$R$_{15}$, wherein $R_{12}$ is as defined above and $R_{13}$, $R_{14}$ and $R_{15}$ are each independently of the other(s) hydrogen or unsubstituted or substituted $C_1$-$C_{18}$alkyl or substituted or unsubstituted aryl, or $R_{13}$ and $R_{14}$, together with the nitrogen atom linking them, form an unsubstituted or substituted 5-, 6- or 7-membered ring which may contain further hetero atoms.

Preference is given to compounds of formula (6a)

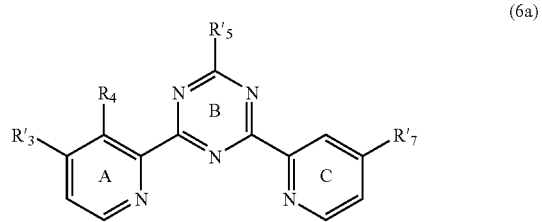

(6a)

wherein R'$_3$ and R'$_7$ have the definitions and preferred meanings indicated above for $R_3$ and $R_7$, and R'$_5$ has the definition and preferred meanings indicated above for $R_5$.

Special preference is given to compounds of formula (6a) wherein

R'$_5$ is $C_1$-$C_4$alkoxy; hydroxy; N-mono- or N,N-di-$C_1$-$C_4$alkylamino substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein $R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, $R_{13}$ and $R_{14}$ are each independently of the other hydrogen; unsubstituted or hydroxy-substituted $C_1$-$C_{12}$alkyl, unsubstituted phenyl or phenyl substituted as indicated above or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrotidine, piperidine, piperazine, morpholine or azepane ring, and R'$_3$ is $C_1$-$C_4$alkoxy; hydroxy; N-mono- or N,N-di-$C_1$-$C_4$alkylamino unsubstituted or substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein $R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, and $R_{13}$ and $R_{14}$ are each independently of the other hydrogen; unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring, and R'$_7$ is hydrogen; $C_1$-$C_4$alkoxy; hydroxy; N-mono- or N,N-di-$C_1$-$C_4$alkylamino substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein $R_{12}$ is hydrogen; $C_1$-$C_{12}$alkyl or unsubstituted or (substituted in the alkyl moiety by hydroxy) N-mono- or N,N-di-$C_1$-$C_4$alkylamino-, N-phenylamino-, N-naphthylamino-, phenyl-, phenoxy- or naphthyloxy-substituted phenyl, and $R_{13}$ and $R_{14}$ are each independently of the other hydrogen; unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring.

The present invention relates also to the novel ligands L of formula (7)

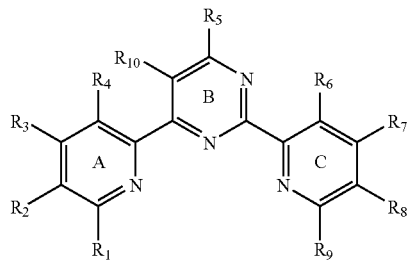

(7)

wherein $R_1$, $R_2$, $R_3$, $R_4$, $R_5$, $R_6$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —COOR$_{11}$ or —SO$_3$R$_{11}$ wherein $R_{11}$ is in each case hydrogen, a cation or unsubstituted or substituted $C_1$-$C_{18}$alkyl or substituted or unsubstituted aryl; —SR$_{12}$, —SO$_2$R$_{12}$ or —OR$_{12}$ wherein $R_{12}$ is in each case hydrogen or unsubstituted or substituted $C_1$-$C_{18}$alkyl or substituted or unsubstituted aryl; —NR$_{13}$R$_{14}$; —(C$_1$-C$_6$alkylene)—NR$_{13}$R$_{14}$; —N$^\oplus$R$_{13}$R$_{14}$R$_{15}$; —(C$_1$-C$_6$alkylene)—N$^\oplus$R$_{13}$R$_{14}$R$_{15}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; —N(R$_{12}$)—(C$_1$-C$_6$alkylene)—N$^\oplus$R$_{13}$R$_{14}$R$_{15}$; —N[(C$_1$-C$_6$alkylene)—N$^\oplus$R$_{13}$R$_{14}$R$_{15}$]$_2$; —N(R$_{12}$)—N—R$_{13}$R$_{14}$; or —N(R$_{12}$)—N$^\oplus$R$_{13}$R$_{14}$R$_{15}$, wherein $R_{12}$ is as defined above and $R_{13}$, $R_{14}$ and $R_{15}$ are each independently of the other(s) hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms, and $R_7$ is phenyl substituted by $C_1$-$C_4$alkyl, $C_1$-$C_4$alkoxy, hydroxy, sulfo, sulfato, halogen, cyano, nitro, carboxy, amino, N-mono- or N,N-di-$C_1$-$C_4$alkylamino unsubstituted or substituted by hydroxy in the alkyl moiety, N-phenylamino, N-naphthylamino, phenyl, phenoxy or by naphthyloxy, substituted $C_1$-$C_{18}$alkyl or unsubstituted or substituted aryl; —CH$_3$; $C_3$-$C_{18}$alkyl; cyano; F; Br; I; nitro; —COOR$_{11}$ or —SO$_3$R$_{11}$ wherein $R_{11}$ is in each case hydrogen, a cation or unsubstituted or substituted $C_1$-$C_{18}$alkyl or substituted or unsubstituted aryl; —SR$_{12}$, —SO$_2$R$_{12}$ or —OR$_{12}$ wherein $R_{12}$ is in each case hydrogen or unsubstituted or substituted $C_1$-$C_{18}$alkyl or unsubstituted or substituted aryl; —NR$_{13}$R$_{14}$; —(C$_1$-C$_6$alkylene)—NR$_{13}$R$_{14}$; —N$^\oplus$R$_{13}$R$_{14}$R$_{15}$; —(C$_1$-C$_6$alkylene)—N$^\oplus$R$_{13}$R$_{14}$R$_{15}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; —N(R$_{12}$)—(C$_1$-C$_6$alkylene)—N$^\oplus$R$_{13}$R$_{14}$R$_{15}$; —N[(C$_1$-C$_6$alkylene)—N$^\oplus$R$_{13}$R$_{14}$R$_{15}$]$_2$; —N(R$_{12}$)—N—R$_{13}$R$_{14}$; or —N(R$_{12}$)—N$^\oplus$R$_{13}$R$_{14}$R$_{15}$, wherein $R_{12}$ is as defined above and $R_{13}$, $R_{14}$ and $R_{15}$ are each independently of the other(s) hydrogen or unsubstituted or substituted $C_1$-$C_{18}$alkyl or substituted or unsubstituted aryl, or $R_{13}$ and $R_{14}$, together with the nitrogen atom linking them, form an unsubstituted or substituted 5-, 6- or 7-membered ring which may contain further hetero atoms.

Preference is given to compounds of formula (7a)

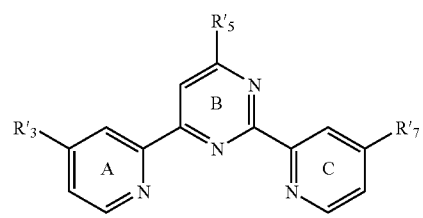

(7a)

wherein R'$_3$ and R'$_7$ have the definitions and preferred meanings indicated above for $R_3$ and $R_7$, and R'$_5$ has the definition and preferred meanings indicated above for $R_5$.

Special preference is given to compounds of formula (7a) wherein

R'$_5$ is $C_1$-$C_4$alkoxy; hydroxy; N-mono- or N,N-di-$C_1$-$C_4$alkylamino substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein $R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, $R_{13}$ and $R_{14}$ are each independently of the other hydrogen; unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring, and R'$_3$ is $C_1$-$C_4$alkoxy; hydroxy; N-mono- or N,N-di-$C_1$-$C_4$alkylamino unsubstituted or substituted by hydroxy in the alkyl moiety; or —NR$_{13}$R$_{14}$; —(C$_1$-C$_6$alkylene)—NR$_{13}$R$_{14}$; —N(R$_{12}$)—(C$_1$-C$_6$alkylene)—NR$_{13}$R$_{14}$; —N[(C$_1$-C$_6$alkylene)—NR$_{13}$R$_{14}$]$_2$; or —N(R$_{12}$)—N—R$_{13}$R$_{14}$, wherein $R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, and $R_{13}$ and $R_{14}$ are each independently of the other hydrogen; unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring, $R'_7$ is hydrogen, $C_1$-$C_4$alkoxy; hydroxy; N-mono- or N,N-di-$C_1$-$C_4$alkylamino substituted by hydroxy in the alkyl moiety; or —$NR_{13}R_{14}$; —($C_1$-$C_6$alkylene)—$NR_{13}R_{14}$; —$N(R_{12})$—($C_1$-$C_6$alkylene)—$NR_{13}R_{14}$; —$N[(C_1$-$C_6$alkylene)—$NR_{13}R_{14}]_2$; or —$N(R_{12})$—N—$R_{13}R_{14}$, wherein $R_{12}$ is hydrogen; $C_1$-$C_{12}$alkyl or unsubstituted phenyl or phenyl substituted by (substituted in the alkyl moiety by hydroxy) N-mono- or N,N-di-$C_1$-$C_4$alkylamino-, N-phenylamino-, N-naphthylamino-, phenyl-, phenoxy- or naphthyloxy, and $R_{13}$ and $R_{14}$ are each independently of the other hydrogen; unsubstituted or hydroxy-substituted $C_1$-$C_{12}$alkyl, unsubstituted phenyl or phenyl substituted as indicated above, or $R_{13}$ and $R_{14}$, together with the nitrogen atom linking them, form a pyrrolidine, piperidine, piperazine, morpholine or azepane ring that is unsubstituted or substituted by at least one unsubstituted $C_1$-$C_4$alkyl and/or substituted $C_1$-$C_4$alkyl, especially a pyrrolidine, piperidine, piperazine, morpholine or azepane ring.

Preferably, the metal complex compounds of formula (1) and/or (1') are used together with peroxy compounds. Examples that may be mentioned in that regard include the following uses:

a) the bleaching of stains or soiling on textile material in the context of a washing process;
b) the prevention of redeposition of migrating dyes during the washing of textile material;
c) the cleaning of hard surfaces, especially kitchen surfaces, wall tiles or floor tiles, for example to remove stains that have formed as a result of the action of moulds ("mould stains");
d) use in washing and cleaning solutions having an antibacterial action;
e) as pretreatment agents for bleaching textiles;
f) as catalysts in selective oxidation reactions in the context of organic synthesis,
g) as catalysts for waste water treatment.

A further use is concerned with the use of at least one metal complex compound of formula (1) and/or (1') as a catalyst for reactions with peroxy compounds for bleaching in the context of paper-making. This relates especially to the delignification of cellulose and bleaching of the pulp, which can be carried out in accordance with customary procedures. Also of interest is the use of at least one metal complex compound of formula (1) and/or (1') as a catalyst for reactions with peroxy compounds for the bleaching of waste printed paper.

Preference is given to the bleaching of stains or soiling on textile material, the prevention of redeposition of migrating dyes in the context of a washing process, or the cleaning of hard surfaces, especially kitchen surfaces, wall tiles or floor tiles. The preferred metals are in this case manganese and/or iron.

It should be emphasised that, for example, in the bleaching of textile material, the metal complex compounds do not cause any appreciable damage to fibres and dyeings.

The metal complexes are also used as catalysts for oxidation reactions using molecular oxygen and/or air.

Processes for preventing the redeposition of migrating dyes in a washing liquor are usually carried out by adding to the washing liquor (which comprises a peroxide-containing detergent) from 0.1 to 200 mg, especially from 1 to 75 mg, more especially from 3 to 50 mg, of one or more metal complex compounds of formula (1) and/or (1') per liter of washing liquor. Alternatively, it is possible to add a detergent that already comprises one or two metal complex compounds. It will be understood that in such an application, as well as in the other applications, the metal complex compounds of formula (1) and/or (1') can alternatively be formed in situ, the metal salt (e.g. manganese(II) salt, such as manganese(II) chloride, and/or iron(II) salt, such as iron(II) chloride) and the ligand being added in the desired molar ratios.

The present invention furthermore relates to a combined process for the prevention of redeposition of migrating dyes and the simultaneous bleaching of stains or soiling on textile material. Metal complexes of formula (1) and/or (1'), especially manganese complexes of formula (1) and/or (1'), are used for that purpose. It is also possible to use manganese complexes of formula (1) and/or (1') together with iron complexes of formula (1) and/or (1').

Processes for the prevention of redeposition of migrating dyes in a washing liquor are usually carried out by adding to the washing liquor (which comprises a peroxide-containing detergent) from 0.1 to 200 mg, especially from 1 to 75 mg, more especially from 3 to 50 mg, per liter of washing liquor, of manganese complexes of formula (1) and/or (1'), optionally together with iron complexes of formula (1) and/or (1'). Alternatively, it is possible to add a composition that already comprises the metal complex mixture in question. It will be understood that in such an application, as well as in the other applications, the metal complex compounds of formula (1) and/or (1') can alternatively be formed in situ, the metal salt (e.g. manganese(II) salt, such as manganese(II) chloride, and/or iron(II) salt, such as iron(II) chloride) and the ligand being added in the desired molar ratios.

The present invention relates also to mixtures of manganese complexes of formula (1) and/or (1') with iron complexes of formula (1) and/or (1').

The present invention relates also to a detergent, cleaning, disinfecting or bleaching composition containing I) from 0 to 50%, preferably from 0 to 30%, A) of an anionic surfactant and/or B) of a non-ionic surfactant,
II) from 0 to 70%, preferably from 0 to 50%, C) of a builder substance,
III) from 1 to 99%, preferably from 1 to 50%, D) of a peroxide or of a peroxide-forming substance,
IV) E) at least one metal complex compound of formula (1) and/or (1') in an amount that, in the liquor, gives a concentration of from 0.5 to 50 mg/liter of liquor, preferably from 1 to 30 mg/liter of liquor, when from 0.5 to 20 g/liter of the detergent, cleaning, disinfecting or bleaching agent are added to the liquor, and
V) water ad 100%.

The present invention relates also to a detergent, cleaning, disinfecting or bleaching composition that is free of peroxide and/or "peroxide-forming substance" and contains I) from 0 to 50% by weight, preferably from 0 to 30% by weight, A) of an anionic surfactant and/or B) of a non-ionic surfactant,
II) from 0 to 70% by weight, preferably from 0 to 50% by weight, C) of a builder substance, III) D) at least one metal complex compound of formula (1) and/or (1') in an amount that, in the liquor, gives a concentration of from 0.5 to 100 mg/liter of liquor, preferably from 1 to 50 mg/liter of liquor, when from 0.5 to 20 g/liter of the detergent, cleaning, disinfecting or bleaching agent are added to the liquor, and IV) water ad 100% by weight.

The above percentages are in each case percentages by weight, based on the total weight of the composition. The compositions preferably contain from 0.005 to 2% of a metal complex compound of formula (1), especially from 0.01 to 1% and preferably from 0.05 to 1%. When the compositions according to the invention comprise a component A) and/or B), the amount thereof is preferably from 1 to 50%, especially from 1 to 30%.

When the compositions according to the invention comprise a component C), the amount thereof is preferably from 1 to 70%, especially from 1 to 50%. Special preference is given to an amount of from 5 to 50% by weight and especially an amount of from 10 to 50%.

Corresponding detergent, cleaning, disinfecting or bleaching processes are usually carried out by using an aqueous liquor comprising a peroxide and from 0.1 to 200 mg of one or more compounds of formula (1) and/or (1') per liter of liquor. Preferably, the liquor contains from 1 to 30 mg of at least one compound of formula (1) and/or (1') per liter of liquor.

The composition according to the invention can be, for example, a peroxide-containing heavy-duty detergent or a separate bleaching additive. A bleaching additive is used in the removal of coloured stains on textiles in a separate liquor, before the clothes are washed with a bleach-free detergent. A bleaching additive can also be used in a liquor together with a bleach-free detergent. Stain removers can be applied directly to the textile in question and are used especially for pretreatment in the event of heavy local soiling. The stain remover can be applied in liquid form, by a spraying method or in the form of a solid substance.

Granules can be prepared, for example, by first preparing an initial powder by spray-drying an aqueous suspension comprising all the components listed above except for components D) and E, and then adding the dry components D) and E) and mixing everything together. It is also possible to add component E) to an aqueous suspension containing components A), B) and C), then carry out spray-drying, and then mix component D) with the dry mass.

It is furthermore possible to start with an aqueous suspension that comprises components A) and C), but none or only some of component B). The suspension is spray-dried, then component E) is mixed with component B) and added, and finally component D) is admixed in the dry state.

It is also possible to mix all the components together in the dry state.

The anionic surfactant A) can be, for example, a sulfate, sulfonate or carboxylate surfactant or a mixture thereof. Preference is given to alkylbenzenesulfonates, alkyl sulfates, alkyl ether sulfates, olefin sulfonates, fatty acid salts, alkyl and alkenyl ether carboxylates or to an α-sulfonic fatty acid salt or an ester thereof.

Preferred sulfonates are, for example, alkylbenzene-sulfonates having from 10 to 20 carbon atoms in the alkyl radical, alkyl sulfates having from 8 to 18 carbon atoms in the alkyl radical, alkyl ether sulfates having from 8 to 18 carbon atoms in the alkyl radical, and fatty acid salts derived from palm oil or tallow and having from 8 to 18 carbon atoms in the alkyl moiety. The average molar number of ethylene oxide units added to the alkyl ether sulfates is from 1 to 20, preferably from 1 to 10. The cation in the anionic surfactants is preferably an alkaline metal cation, especially sodium or potassium, more especially sodium. Preferred carboxylates are alkali metal sarcosinates of formula $R_{19}$—$CON(R_{20})CH_2COOM_1$ wherein $R_{19}$ is $C_9$-$C_{17}$alkyl or $C_9$-$C_{17}$alkenyl, $R_{20}$ is $C_1$-$C_4$alkyl and $M_1$ is an alkali metal, especially sodium.

The non-ionic surfactant B) may be, for example, a primary or secondary alcohol ethoxylate, especially a $C_8$-$C_{20}$ aliphatic alcohol, ethoxylated with an average of from 1 to 20 mol of ethylene oxide per alcohol group. Preference is given to primary and secondary $C_{10}$-$C_{15}$ aliphatic alcohols ethoxylated with an average of from 1 to 10 mol of ethylene oxide per alcohol group. Non-ethoxylated non-ionic surfactants, for example alkylpolyglycosides, glycerol monoethers and polyhydroxyamides (glucamide), may likewise be used.

The total amount of anionic and non-ionic surfactants is preferably from 5 to 50% by weight, especially from 5 to 40% by weight and more especially from 5 to 30% by weight. The lower limit of those surfactants to which even greater preference is given is 10% by weight.

As builder substance C) there come into consideration, for example, alkali metal phosphates, especially tripolyphosphates, carbonates and hydrogen carbonates, especially their sodium salts, silicates, aluminum silicates, polycarboxylates, polycarboxylic acids, organic phosphonates, aminoalkylenepoly(alkylenephosphonates) and mixtures of such compounds.

Silicates that are especially suitable are sodium salts of crystalline layered silicates of the formula $NaHSi_tO_{2t+1} \cdot pH_2O$ or $Na_2Si_tO_{2t+1} \cdot pH_2O$ wherein t is a number from 1.9 to 4 and p is a number from 0 to 20.

Among the aluminum silicates, preference is given to those commercially available under the names zeolite A, B, X and HS, and also to mixtures comprising two or more such components. Special preference is given to zeolite A.

Among the polycarboxylates, preference is given to polyhydroxycarboxylates, especially citrates, and acrylates, and also to copolymers thereof with maleic anhydride. Preferred polycarboxylic acids are nitrilotriacetic acid, ethylenediaminetetraacetic acid and ethylenediamine disuccinate either in racemic form or in the enantiomerically pure (S,S) form.

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid and diethylenetriaminepentamethylenephosphonic acid, and also salts thereof.

Suitable peroxides include, for example, organic and inorganic peroxides (for example sodium peroxide), which are known from the literature and are commercially available and bleach textile materials at the usual washing temperatures (5-95° C.).

Organic peroxides to which preference is given are, for example, mono- or poly-peroxides having at least 3 carbon atoms, preferably from 6 to 20 carbon atoms, in the alkyl chain. Greater preference is given to diperoxydicarboxylates having from 6 to 12 carbon atoms, for example diperoxyperacetates, diperoxypersebacates diperoxyphthalates and diperoxydodecanedioates, emphasis being given especially to the free acids thereof.

Special preference is given, for example, to mono- and poly-peroxides, especially organic peracids or salts thereof, such as phthalimidoperoxycaproic acid, peroxybenzoic acid, diperoxydodecanedioic acid, diperoxynonanedioic acid, diperoxydecanedioic acid, diperoxyphthalic acid and salts thereof.

The total content of peroxides is preferably from 0.5 to 30% by weight, especially from 1 to 20% by weight and more especially from 1 to 15% by weight. When a peroxide is used, greater preference is given to a lower limit of 2% by weight, especially 5% by weight.

It is preferred, however, to use inorganic peroxides, for example persulfates, perborates, percarbonates and/or persilicates. It will be understood that it is also possible to use mixtures of inorganic and/or organic peroxides. The peroxides may be in various crystalline forms and with a varying water content, and they may also be used together with other inorganic or organic compounds in order to improve their storage stability.

The addition of peroxides to the composition is preferably carried out by mixing the components together, for example using a screw metering system and/or a fluidised bed mixer.

The compositions may, in addition to comprising the combination according to the invention, comprise one or more optical brighteners, for example from the classes bis-triazinylamino-stilbenedisulfonic acid, bis-triazolyl-stilbenedisulfonic acid, bis-styryl-biphenyl or bis-benzofuranylbiphenyl, a bis-benzoxalyl derivative, bis-benzimidazolyl derivative or coumarin derivative or a pyrazoline derivative.

The compositions may furthermore comprise one or more auxiliaries. Such auxiliaries are, for example, dirt-suspending agents, for example sodium carboxymethylcellulose; pH regulators, for example alkali metal or alkaline earth metal silicates; foam regulators, for example soap; salts for adjusting the spray drying and the granulating properties, for example sodium sulfate; perfumes; and also, if appropriate, antistatics and softening agents such as, for example, smectite; bleaching agents; pigments; and/or toning agents. These constituents should especially be stable to any bleaching agent employed.

Such auxiliaries are added in a total amount of from 0.1 to 20% by weight, especially from 0.5 to 10% by weight, more especially from 0.5 to 5% by weight, based on the total weight of the detergent formulation.

Furthermore, the detergent may optionally also comprise enzymes. Enzymes can be added for the purpose of stain removal. The enzymes usually improve the action on stains caused by protein or starch, such as, for example, blood, milk, grass or fruit juices. Preferred enzymes are cellulases and proteases, especially proteases. Cellulases are enzymes that react with cellulose and its derivatives and hydrolyse them to form glucose, cellobiose and cellooligosaccharides. Cellulases remove dirt and, in addition, have the effect of enhancing the soft handle of the fabric.

Examples of customary enzymes include, but are by no means limited to, the following:
proteases as described in U.S. Pat. No. 6,242,405, column 14, lines 21 to 32;
lipases as described in U.S. Pat. No. 6,242,405, column 14, lines 33 to 46;
amylases as described in U.S. Pat. No. 6,242,405, column 14, lines 47 to 56; and
cellulases as described in U.S. Pat. No. 6,242,405, column 14, lines 57 to 64.

The enzymes, when used, may be present in a total amount of from 0.01 to 5% by weight, especially from 0.05 to 5% by weight and more especially from 0.1 to 4% by weight, based on the total weight of the detergent formulation.

In order to enhance the bleaching action, the compositions may, in addition to comprising the catalysts described herein, also comprise photocatalysts the action of which is based on the generation of singlet oxygen.

In addition to using the bleach catalyst according to formula (1) and/or (1'), it is also possible to use further transition metal salts or complexes known as bleach-activating active substances and/or to use conventional bleach activators, that is, compounds that, under the conditions of perhydrolysis, yield unsubstituted or substituted perbenzo- and/or peroxo-carboxylic acids having from 1 to 10 carbon atoms, especially from 2 to 4 carbon atoms. The customary bleach activators mentioned earlier, which contain O- and/or N-acyl groups having the mentioned number of carbon atoms and/or unsubstituted or substituted benzoyl groups, are suitable. Preference is given to polyacylated alkylenediamines, especially tetraacetylethylenediamine (TAED), acylated glycourils, especially tetraacetylglycoluril (TAGU), N,N-diacetyl-N,N-dimethylurea (DDU), acylated triazine derivatives, especially 1,5-diacetyl-2,4-dioxohexahydro-1,3,5-triazine (DADHT), compounds of formula (8):

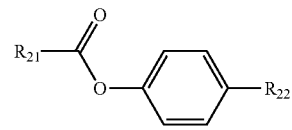

(8)

wherein $R_{21}$ is a sulfonate group, a carboxylic acid group or a carboxylate group and wherein $R_{22}$ is a linear or branched $(C_7-C_{15})$alkyl, especially activators known under the names SNOBS, SLOBS and DOBA, acylated polyhydric alcohols, especially triacetin, ethylene glycol diacetate and 2,5-diacetoxy-2,5-dihydrofuran and also acetylated sorbitol and mannitol and acylated sugar derivatives, especially pentaacetyl glucose (PAG), sucrose polyacetate (SUPA), pentaacetyl fructose, tetraacetyl xylose and octaacetyl lactose, as well as acetylated, optionally N-alkylated glucamine and gluconolactone. Conventional bleach-activator combinations known from German Patent Application DE-A-44 43 177 may also be used. As bleach activators, there also come into consideration nitrile compounds that with peroxides form perimine acids.

Further preferred additives to the compositions according to the invention are dye-fixing agents and/or polymers which, during the washing of textiles, prevent staining caused by dyes in the washing liquor that have been released from the textiles under the washing conditions. Such polymers are preferably polyvinylpyrrolidones, polyvinylimidazoles or polyvinylpyridine-N-oxides, which may have been modified by the incorporation of anionic or cationic substituents, especially those having a molecular weight in the range of from 5000 to 60 000, more especially from 10 000 to 50 000. Such polymers are usually used in a total amount of from 0.01 to 5% by weight, especially from 0.05 to 5% by weight, more especially from 0.1 to 2% by weight, based on the total weight of the detergent formulation. Preferred polymers are those mentioned in WO-A-02/02865 (see especially page 1, last paragraph and page 2, first paragraph).

The detergent formulations can take a variety of physical forms such as, for example, powder, granule, tablets (tabs) and liquid. Examples thereof include, inter alia, conventional high-performance detergent powders, supercompact high-performance detergent powders and tabs. One important physical form is the so-called concentrated granular form, which is added to a washing machine.

Also of importance are so-called compact or supercompact detergents. In the field of detergent manufacture, there is a trend towards the production of such detergents that contain an increased amount of active substances. In order to minimize energy consumption during the washing procedure, compact or supercompact detergents need to act effectively at low washing temperatures, for example below 40° C. or even at room temperature (25° C.). Such detergents usually contain only small amounts of fillers or of substances, such as sodium sulfate or sodium chloride, required for detergent manufacture. The total amount of such substances is usually from 0 to 10% by weight, especially from 0 to 5% by weight, and more especially from 0 to 1% by weight, based on the total weight of the detergent formulation. Such (super)compact detergents usually have a bulk density of from 650 to 1000 g/l, especially from 700 to 1000 g/l and more especially from 750 to 1000 g/l. The detergent formulations can also be in the form of tablets (tabs). The advantages of tabs reside in the ease of dispensing and convenience in handling. Tabs are the most compact form of solid detergent formulation and usually have a volumetric density of, for example, from 0.9 to 1.3 kg/liter. To achieve rapid dissolution, such tabs generally contain special dissolution aids:
- carbonate/hydrogen carbonate/citric acid as effervescents;
- disintegrators, such as cellulose, carboxymethyl cellulose or cross-linked poly(N-vinylpyrrolidone);
- rapidly dissolving materials, such as sodium (potassium) acetates, or sodium (potassium) citrates;
- rapidly dissolving, water-soluble, rigid coating agents, such as dicarboxylic acids.

The tabs may also comprise combinations of such dissolution aids.

The detergent formulation may also be in the form of an aqueous liquid containing from 5 to 50% by weight, preferably from 10 to 35% by weight, of water or in the form of a non-aqueous liquid containing no more than 5% by weight, preferably from 0 to 1% by weight, of water. Non-aqueous liquid detergent formulations may comprise other solvents as carriers. Low molecular weight primary or secondary alcohols, for example methanol, ethanol, propanol and iso-propanol, are suitable for that purpose. The solubilising surfactant used is preferably a monohydroxy alcohol but polyols, such as those containing from 2 to 6 carbon atoms and from 2 to 6 hydroxy groups, for example 1,3-propanediol, ethylene glycol, glycerol and 1,2-propanediol, can also be used. Such carriers are usually used in a total amount of from 5% to 90% by weight, preferably from 10% to 50% by weight, based on the total weight of the detergent formulation. The detergent formulations can also used in so-called "unit liquid dose" form.

The invention relates also to granules that comprise the catalysts according to the invention and are suitable for incorporation into a powder-form or granular detergent, cleaning or bleaching composition. Such granules preferably comprise:
a) from 1 to 99% by weight, preferably from 1 to 40% by weight, and especially from 1 to 30% by weight, of at least one metal complex compound of formula (1) and/or (1'),
b) from 1 to 99% by weight, preferably from 10 to 99% by weight, and especially from 20 to 80% by weight, of a binder,
c) from 0 to 20% by weight, especially from 1 to 20% by weight, of an encapsulating material,
d) from 0 to 20% by weight of a further additive and
e) from 0 to 20% by weight of water.

As binder (b) there come into consideration water-soluble, dispersible or water-emulsifiable anionic dispersants, non-ionic dispersants, polymers and waxes.

The anionic dispersants used are, for example, commercially available water-soluble anionic dispersants for dyes, pigments etc.

The following products, especially, come into consideration: condensation products of aromatic sulfonic acids and formaldehyde, condensation products of aromatic sulfonic acids with unsubstituted or chlorinated diphenyls or diphenyl oxides and optionally formaldehyde, (mono-/di-)alkyl-naphthalenesulfonates, sodium salts of polymerised organic sulfonic acids, sodium salts of polymerised alkylnaphthalenesulfonic acids, sodium salts of polymerised alkylbenzenesulfonic acids, alkylarylsulfonates, sodium salts of alkyl polyglycol ether sulfates, polyalkylated polynuclear arylsulfonates, methylene-linked condensation products of arylsulfonic acids and hydroxyarylsulfonic acids, sodium salts of dialkylsulfosuccinic acid, sodium salts of alkyl diglycol ether sulfates, sodium salts of polynaphthalenemethanesulfonates, lignosulfonates or oxylignosulfonates and heterocyclic polysulfonic acids. Especially suitable anionic dispersants are condensation products of naphthalene-sulfonic acids with formaldehyde, sodium salts of polymerised organic sulfonic acids, (mono-/di-)alkylnaphthalene-sulfonates, polyalkylated polynuclear arylsulfonates, sodium salts of polymerised alkylbenzenesulfonic acid, lignosulfonates, oxylignosulfonates and condensation products of naphthalenesulfonic acid with a polychloromethyl-diphenyl.

Suitable non-ionic dispersants are especially compounds having a melting point of, preferably, at least 35° C. that are emulsifiable, dispersible or soluble in water, for example the following compounds:

1. fatty alcohols having from 8 to 22 carbon atoms, especially cetyl alcohol;
2. addition products of, preferably, from 2 to 80 mol of alkylene oxide, especially ethylene oxide, wherein some of the ethylene oxide units may have been replaced by substituted epoxides, such as styrene oxide and/or propylene oxide, with higher unsaturated or saturated monoalcohols, fatty acids, fatty amines or fatty amides having from 8 to 22 carbon atoms or with benzyl alcohols, phenyl phenols, benzyl phenols or alkyl phenols, the alkyl radicals of which have at least 4 carbon atoms;
3. alkylene oxide, especially propylene oxide, condensation products (block polymers);
4. ethylene oxide/propylene oxide adducts with diamines, especially ethylenediamine;
5. reaction products of a fatty acid having from 8 to 22 carbon atoms and a primary or secondary amine having at least one hydroxy-lower alkyl or lower alkoxy-lower alkyl group, or alkylene oxide addition products of such hydroxyalkyl-group-containing reaction products;
6. sorbitan esters, preferably having long-chain ester groups, or ethoxylated sorbitan esters, such as polyoxyethylene sorbitan monolaurate having from 4 to 10 ethylene oxide units or polyoxyethylene sorbitan trioleate having from 4 to 20 ethylene oxide units;
7. addition products of propylene oxide with a tri- to hexa-hydric aliphatic alcohol having from 3 to 6 carbon atoms, e.g. glycerol or pentaerythritol; and 8. fatty alcohol polyglycol mixed ethers, especially addition products of from 3 to 30 mol of ethylene oxide and from 3 to 30 mol of propylene oxide with aliphatic monoalcohols having from 8 to 22 carbon atoms.

Especially suitable non-ionic dispersants are surfactants of formula $$R_{23}\text{—}O\text{—}(\text{alkylene-}O)_n\text{—}R_{24} \quad (9),$$

wherein
$R_{23}$ is $C_8$-$C_{22}$alkyl or $C_8$-$C_{18}$alkenyl;
$R_{24}$ is hydrogen; $C_1$-$C_4$alkyl; a cycloaliphatic radical having at least 6 carbon atoms; or benzyl;
"alkylene" is an alkylene radical having from 2 to 4 carbon atoms and
n is a number from 1 to 60.

The substituents $R_{23}$ and $R_{24}$ in formula (9) are advantageously each the hydrocarbon radical of an unsaturated or, preferably, saturated aliphatic monoalcohol having from 8 to 22 carbon atoms. The hydrocarbon radical may be straight-chain or branched.

$R_{23}$ and $R_{24}$ are preferably each independently of the other an alkyl radical having from 9 to 14 carbon atoms.

Aliphatic saturated monoalcohols that may into consideration include natural alcohols, e.g. lauryl alcohol, myristyl alcohol, cetyl alcohol or stearyl alcohol, and also synthetic alcohols, e.g. 2-ethylhexanol, 1,1,3,3-tetramethylbutanol, octan-2-ol, isononyl alcohol, trimethylhexanol, trimethylnonyl alcohol, decanol, $C_9$-$C_{11}$oxo-alcohol, tridecyl alcohol, isotridecyl alcohol and linear primary alcohols (Alfols) having from 8 to 22 carbon atoms. Some examples of such Alfols are Alfol (8-10), Alfol (9-11), Alfol (10-14), Alfol (12-13) and Alfol (16-18). ("Afol" is a registered trade mark of the company Sasol Limited).

Unsaturated aliphatic monoalcohols are, for example, dodecenyl alcohol, hexadecenyl alcohol and oleyl alcohol.

The alcohol radicals may be present singly or in the form of mixtures of two or more components, e.g. mixtures of alkyl and/or alkenyl groups that are derived from soybean fatty acids, palm kernel fatty acids or tallow oils.

(Alkylene-O) chains are preferably bivalent radicals of the formulae

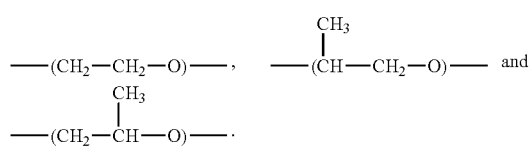

Examples of a cycloaliphatic radical include cycloheptyl, cyclooctyl and, preferably, cyclohexyl.

As non-ionic dispersants there come into consideration preferably surfactants of formula

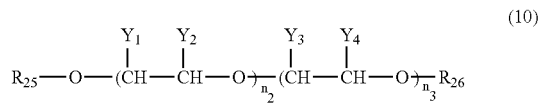

wherein
$R_{25}$ is $C_8$-$C_{22}$alkyl;
$R_{26}$ is hydrogen or $C_1$-$C_4$alkyl;
$Y_1$, $Y_2$, $Y_3$ and $Y_4$ are each independently of the others hydrogen, methyl or ethyl;

$n_2$ is a number from 0 to 8; and
$n_3$ is a number from 2 to 40.

Further important non-ionic dispersants correspond to formula

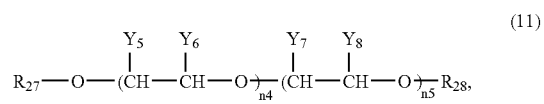

wherein
$R_{27}$ is $C_9$-$C_{14}$alkyl;
$R_{28}$ is $C_1$-$C_4$alkyl;
$Y_5$, $Y_6$, $Y_7$ and $Y_8$ are each independently of the others hydrogen, methyl or ethyl, one of the radicals $Y_5$, $Y_6$ and one of the radicals $Y_7$, $Y_8$ always being hydrogen; and
$n_4$ and $n_5$ are each independently of the other an integer from 4 to 8.

The non-ionic dispersants of formulae (9) to (11) can be used in the form of mixtures. For example, as surfactant mixtures there come into consideration non-end-group-terminated fatty alcohol ethoxylates of formula (9), e.g. compounds of formula (9) wherein
$R_{23}$ is $C_8$-$C_{22}$alkyl,
$R_{24}$ is hydrogen and
the alkylene-O chain is the radical —($CH_2$—$CH_2$—O)—,
and also end-group-terminated fatty alcohol ethoxylates of formula (11).

Examples of non-ionic dispersants of formulae (9), (10) and (11) include reaction products of a $C_{10}$-$C_{13}$fatty alcohol, e.g. a $C_{13}$oxo-alcohol, with from 3 to 10 mol of ethylene oxide, propylene oxide and/or butylene oxide and the reaction product of one mol of a $C_{13}$fatty alcohol with 6 mol of ethylene oxide and 1 mol of butylene oxide, it being possible for the addition products each to be end-group-terminated with $C_1$-$C_4$alkyl, preferably methyl or butyl.

Such dispersants can be used singly or in the form of mixtures of two or more dispersants.

Instead of, or in addition to, the anionic or non-ionic dispersant, the granules according to the invention may comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain (α-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinylpyrrolidone/dimethylaminoethyl methacrylates, copolymers of styrene and acrylic acid, polycarboxylic acids, polyacrylamides, carboxymethyl cellulose, hydroxymethyl cellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxymethyl cellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolymers of ethyl acrylate with methacrylate and methacrylic acid, and polymethacrylates.

Suitable water-emulsifiable or water-dispersible binders also include paraffin waxes.

Encapsulating materials (c) include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents.

The preparation of the granules according to the invention is carried out, for example, starting from:
a) a solution or suspension with a subsequent drying/shaping step or
b) a suspension of the active ingredient in a melt with subsequent shaping and solidification.
a) First of all the anionic or non-ionic dispersant and/or the polymer and, optionally, the further additives are dissolved in water and stirred, if desired with heating, until a homogeneous solution is obtained. The catalyst according to the invention is then dissolved or suspended in the resulting aqueous solution. The solids content of the solution should preferably be at least 30% by weight, especially from 40 to 50% by weight, based on the total weight of the solution. The viscosity of the solution is preferably less than 200 mPas.

The aqueous solution so prepared, comprising the catalyst according to the invention, is then subjected to a drying step in which all water, with the exception of a residual amount, is removed, solid particles (granules) being formed at the same time. Known methods are suitable for producing the granules from the aqueous solution. In principle, both continuous methods and discontinuous methods are suitable. Continuous methods are preferred, especially spray-drying and fluidised bed granulation processes.

Especially suitable are spray-drying processes in which the active ingredient solution is sprayed into a chamber with circulating hot air. The atomisation of the solution is effected e.g. using unitary or binary nozzles or is brought about by the spinning effect of a rapidly rotating disc. In order to increase the particle size, the spray-drying process may be combined with an additional agglomeration of the liquid particles with solid nuclei in a fluidised bed that forms an integral part of the chamber (so-called fluid spray). The fine particles (<100 µm) obtained by a conventional spray-drying process may, if necessary after being separated from the exhaust gas flow, be fed as nuclei, without further treatment, directly into the atomizing cone of the atomiser of the spray-dryer for the purpose of agglomeration with the liquid droplets of the active ingredient.

During the granulation step, the water can rapidly be removed from the solutions comprising the catalyst according to the invention, binder and further additives. It is expressly intended that agglomeration of the droplets forming in the atomising cone, or agglomeration of droplets with solid particles, will take place.

If necessary, the granules formed in the spray-dryer are removed in a continuous process, for example by a sieving operation. The fines and the oversize particles are either recycled directly to the process (without being redissolved) or are dissolved in the liquid active ingredient formulation and subsequently granulated again.

A further preparation method according to a) is a process in which the polymer is mixed with water and then the catalyst is dissolved/suspended in the polymer solution, thus forming an aqueous phase, the catalyst according to the invention being homogeneously distributed in that phase. At the same time or subsequently, the aqueous phase is dispersed in a water-immiscible liquid in the presence of a dispersion stabiliser in order that a stable dispersion is formed. The water is then removed from the dispersion by distillation, forming substantially dry particles. In those particles, the catalyst is homogeneously distributed in the polymer matrix.

The granules according to the invention are resistant to abrasion, low in dust, pourable and readily meterable. They can be added directly to a formulation, such as a detergent formulation, in the desired concentration of the catalyst according to the invention.

Where the coloured appearance of the granules in the detergent is to be suppressed, this can be achieved, for example, by embedding the granules in a droplet of a whitish meltable substance ("water-soluble wax") or by adding a white pigment (e.g. $TiO_2$) to the granule formulation or, preferably, by encapsulating the granules in a melt consisting, for example, of a water-soluble wax, as described in EP-A-0 323 407, a white solid being added to the melt in order to reinforce the masking effect of the capsule.

b) The catalyst according to the invention is dried in a separate step prior to the melt-granulation and, if necessary, dry-ground in a mill so that all the solids particles are <50 µm in size. The drying is carried out in an apparatus customary for the purpose, for example in a paddle dryer, vacuum cabinet or freeze-dryer.

The finely particulate catalyst is suspended in the molten carrier material and homogenised. The desired granules are produced from the suspension in a shaping step with simultaneous solidification of the melt. The choice of a suitable melt-granulation process is made in accordance with the desired size of granules. In principle, any process which can be used to produce granules in a particle size of from 0.1 to 4 mm is suitable. Such processes are droplet processes (with solidification on a cooling belt or during free fall in cold air), melt-prilling (gas/liquid cooling medium), and flake formation with a subsequent comminution step, the granulation apparatus being operated continuously or discontinuously.

Where the coloured appearance of the granules prepared from a melt is to be suppressed in the detergent, in addition to the catalyst it is also possible to suspend in the melt white or coloured pigments which, after solidification, impart the desired coloured appearance to the granules (e.g. titanium dioxide).

If desired, the granules can be covered with or encapsulated in an encapsulating material. Methods that come into consideration for such an encapsulation include the customary methods and also encapsulation of the granules by a melt consisting e.g. of a water-soluble wax, as described, for example, in EP-A-0 323 407, coacervation, complex coacervation and surface polymerisation.

Encapsulating materials (c) include e.g. water-soluble, water-dispersible or water-emulsifiable polymers and waxes.

As further additives (d) there come into consideration, for example, wetting agents, dust removers, water-insoluble or water-soluble dyes or pigments, and also dissolution accelerators, optical brighteners and sequestering agents.

Surprisingly, the metal complex compounds of formula (1) and/or (1') also exhibit a markedly improved bleach-catalysing action on coloured stains occurring, for example, on wall tiles or floor tiles.

The use of at least one metal complex compound of formula (1) and/or (1') as catalyst(s) for reactions with peroxy compounds in cleaning solutions for hard surfaces, especially wall tiles or floor tiles, is therefore of special interest.

The metal complex compounds of formula (1) and/or (1') together with peroxy compounds furthermore have excellent antibacterial action. The use of at least one metal complex compound of formula (1) and/or (1') for killing bacteria or for protecting against bacterial attack is therefore likewise of interest.

The metal complex compounds of formula (1) and/or (1') are also outstandingly suitable for selective oxidation in the context of organic synthesis, especially the oxidation of organic molecules, e.g. of olefins to form epoxides. Such selective transformation reactions are required especially in process chemistry. The invention accordingly relates also to the use of at least one metal complex compound of formula (1) and/or (1') in selective oxidation reactions in the context of organic synthesis.

The following Examples serve to illustrate the invention but do not limit the invention thereto. Parts and percentages relate to weight, unless otherwise indicated. Temperatures are in degrees Celsius, unless otherwise indicated.

Synthesis of Compounds of the Pyrimidine Type

EXAMPLE 1

4-Chloropyridine-2-carboxylic acid ethyl ester

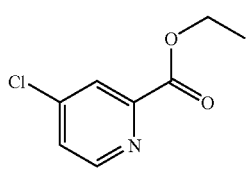

a) Step 1:

10.0 ml of (0.130 mol) of N,N-dimethylformamide are added dropwise at 40° C., with stirring, to 295 ml (4.06 mol) of thionyl chloride. Then, in the course of half an hour, 100 g (0.812 mol) of picolinic acid are added. The mixture is cautiously heated to 70° C. and stirred at that temperature for 24 hours, the gases formed being conveyed away through a wash bottle charged with sodium hydroxide solution. Concentration, and coevaporation a further three times with 100 ml of toluene each time, are carried out; the product is diluted with that solvent to 440 ml, and the solution is introduced into a mixture of 120 ml of absolute ethanol and 120 ml of toluene. The mixture is concentrated to approximately half its volume, cooled to 4° C., filtered off under suction and washed with toluene. 4-Chloropyridine-2-carboxylic acid ethyl ester hydrochloride is obtained in the form of a beige hygroscopic powder.

b) Step 2:

The hydrochloride obtained in Step 1 is taken up in 300 ml of ethyl acetate and 200 ml of deionised water and rendered neutral with 4N sodium hydroxide solution. After separation of the phases, extraction is carried out twice with 200 ml of ethyl acetate each time. The organic phases are combined, dried over sodium sulfate, filtered and concentrated. 4-Chloropyridine-2-carboxylic acid ethyl ester is obtained in the form of a brown oil which, if required, can be purified by distillation.

$^1$H-NMR (360 MHz, CDCl$_3$): 8.56 (d, J=5.0 Hz, 1H); 8.03 (d, J=1.8 Hz, 1H); 7.39 (dd, J=5.4,1.8 Hz, 1H); 4.39 (q, J=7.0 Hz, 2H); 1.35 (t, 3 H, J=7.0 Hz).

EXAMPLE 2

3-(4-Chloropyrid-2-yl)-3-oxopropionic acid ethyl ester

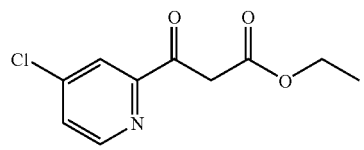

Under a nitrogen atmosphere, 4 g (approximately 60% dispersion in paraffin oil, about 100 mmol) of sodium hydride are washed twice with 60 ml of n-hexane each time, and then 400 ml of absolute tetrahydrofuran are added. The mixture is heated to 50° C. and, in the course of 2 hours, a solution of 13.36 g (72 mmol) of 4-chloropyridine-2-carboxylic acid ethyl ester and 10.04 g (114 mmol) of ethyl acetate in 60 ml of absolute tetrahydrofuran is added dropwise, during which the mixture begins to boil vigorously. When the exothermic reaction has subsided, stirring is carried out for 12 hours at room temperature to complete the reaction. The yellow suspension is poured into 400 ml of ice-water and rendered neutral with 15% hydrochloric acid, and the solution is concentrated to half its volume. Extraction is then carried out twice with 200 ml of ethyl acetate each time, and the organic extracts are combined, dried (sodium sulfate), filtered and concentrated. 14.5 g of 3-(4-chloropyrid-2-yl)-3-oxopropionic acid ethyl ester are obtained in the form of a light-brown oil, which is used for further syntheses without further purification.

$^1$H-NMR (360 MHz, CDCl$_3$): [12.33 (s, 1H, enol)]; 8.53 (d, J=5.4 Hz, 1H) [8.48 (d, J=5.4 Hz, 1H, enol)]; 8.02 (d, J=2.3 Hz, 1H) [7.88 (d, J=1.8 Hz, 1H, enol)]; 7.49-7.44 (qm, 2 H) [7.35-7.30 (qm, 1H, enol)]; [6.31 (s, 1H, enol)]; 4.19-4.11 (m, 4H) [4.29-4.22 (qm, 2H, enol)]; 1.24-1.17 (tm, 3H) [1.33-1.27 (tm, 3H, enol)].

EXAMPLE 3

6-(4-Chloropyrid-2-yl)-2-pyrid-2-yl-pyrimidin-4-ol (ligand PM1)

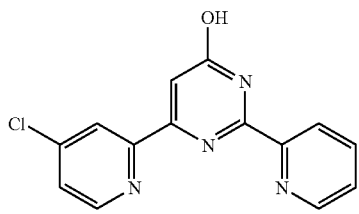

13.15 g (58 mmol) of 3-(4-chloropyrid-2-yl)-3-oxopropionic acid ethyl ester are dissolved in 400 ml of ethanol, and 9.10 g (58 mmol) of 2-amidinopyridine hydrochloride are added. After the addition of 14.44 ml of 4N sodium hydroxide solution, refluxing is carried out for 7 hours. The mixture is cooled and concentrated to a fifth of its original volume. The crude product is filtered off and recrystallised from methanol, yielding 6-(4-chloropyrid-2-yl)-2-pyrid-2-yl-pyrimidin-4-ol in the form of beige needles.

$^1$H-NMR (360 MHz, CDCl$_3$): 12.33 (br s, 1H); 8.76 (d, J=4.5 Hz, 1H); 8.69 (d, J=5.4 Hz, 1H); 8.62 (d, J=7.7 Hz, 1H); 8.50 (d, J=1.8 Hz, 1H); 8.15-8.03 (tm, 1H); 7.75-7.63 (m, 2H); 7.25 (s, 1H).

EXAMPLE 4

6-[4-(4-methyl-piperazin-1-yl)-pyrid-2-yl]-2-pyrid-2-yl-pyrimidin-4-ol (ligand PM2)

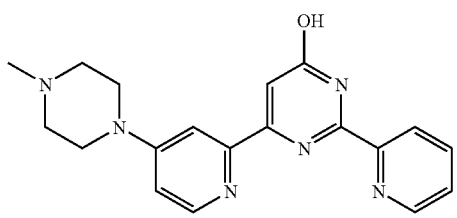

A mixture of 3.51 g (12.3 mmol) of 6-(4-chloropyrid-2-yl)-2-pyrid-2-yl-pyrimidin-4-ol, 27.4 ml (303 mmol, 20 equivalents, 30.38 g) of 1-methyl-piperazine and 84 mg (0.05 mmol, 0.05 equivalent) of zinc(II) chloride in 50 ml of 2-methyl-2-butanol is refluxed for 22 hours and concentrated to dryness using a rotary evaporator. 50 ml of water are added, 3.6 g of EDTA are added, and the pH is adjusted to 9 using dilute sodium hydroxide solution. Extraction is carried out three times using 150 ml of chloroform each time, and the organic extracts are combined and dried (sodium sulfate). Concentration is carried out using a rotary evaporator and the crude product is recrystallised from toluene. 6-[4-(4-Methyl-piperazin-1-yl)-pyrid-2-yl]-2-pyrid-2-yl-pyrimidin-4-ol is obtained in the form of a whitish solid.

$^1$H-NMR (360 MHz, CDCl$_3$): 10.99 (br s, 1H); 8.56 (d, J=4.1 Hz, 1H); 8.44 (d, J=7.7 Hz, 1H); 8.25 (d, J=5.9 Hz, 1H); 7.91-7.81 (tm, 1H); 7.78 (s, 1H); 7.48-7.33 (tm, 1 H); 6.66-6.56 (m, 1H); 3.39 (t, J=5.0 Hz, 4H); 2.53 (t, J=5.0 Hz, 4H); 2.30 (s, 3H).

EXAMPLE 5

Quaternisation of 6-[4-(4-methyl-piperazin-1-yl)-pyrid-2-yl]-2-pyrid-2-yl-pyrimidin-4-ol with Methyl Iodide to Form Ligand PM3

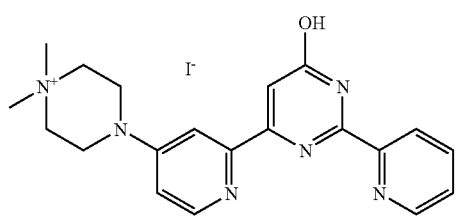

417 mg (2.94 mmol, 0.98 equivalent) of methyl iodide are added dropwise to a suspension of 1.045 g (3 mmol) of 6-[4-(4-methyl-piperazin-1-yl)-pyrid-2-yl]-2-pyrid-2-yl-pyrimidin-4-ol in 20 ml of acetonitrile. The mixture is stirred for 14 hours at room temperature, then heated to 60° C. for 10 minutes and cooled, and the resulting quaternised 6-[4-(4-methyl-piperazin-1-yl)-pyrid-2-yl]-2-pyrid-2-yl-pyrimidin-4-ol is filtered off in the form of a white powder.

$^1$H-NMR (360 MHz, D$_2$O): 8.33 (d, J=4.5 Hz, 1H); 7.73-7.64 (m, 1H); 7.64-7.56 (m, 1H); 7.42-7.31 (m, 2H); 6.78 (d, 2.3 Hz, 1 H); 6.33 (s, 1H); 6.31-6.26 (m, 1H).

EXAMPLE 6

2,6-Di(2-pyridyl)-4-pyrimidinol (Ligand PM4)

(Obtainable from Bionet, Order No. 11G-917)

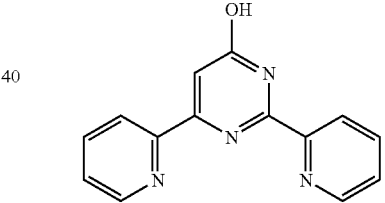

ESI-MS: m/z=251 [M+H]$^+$.

EXAMPLE 7

4-Chloro-2-cyanopyridine

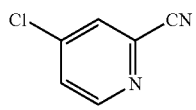

5.0 ml (0.16 equivalent) of N,N-dimethylformamide are added dropwise at 40° C., with stirring, to 150 ml (2.06 mol) of thionyl chloride. Then, in the course of half an hour, 50 g (0.406 mol) of picolinic acid are added. The mixture is cautiously heated to 70° C. and stirred at that temperature for 24 hours, the gases formed being conveyed away through a wash bottle charged with sodium hydroxide solution. Concentration, and coevaporation a further three times with 50 ml of toluene each time, are carried out. 300 ml of diethyl ether are added to the acid chloride-hydrochloride so obtained. The mixture is cooled to 0° C. using an ice/water bath, and 250 ml of 25% ammonium hydroxide solution are cautiously added. The mixture is warmed to room temperature and stirred for 16 hours to complete the reaction. Filtration is carried out, and the filter residue is boiled in 400 ml of chloroform to remove secondary products and recrystallised from 350 ml of methanol. 4-Chloro-2-picolinic acid amide is obtained in the form of a yellowish solid, which is reacted without further purification. 31.3 g (0.2 mol) of the amide obtained in that manner are suspended in 490 ml of dichloromethane and cooled to 0° C. using an ice/water bath. After the addition of 46.5 ml of N,N-dimethylformamide, 36.7 ml of phosphorus oxychloride are added dropwise in the course of 20 minutes while maintaining the temperature, and stirring is carried out for a further 6 hours with cooling. 100 ml of water are then added and the mixture is rendered neutral with 4N sodium hydroxide solution and stirred overnight at room temperature. The organic solvent is removed using a rotary evaporator, and the aqueous phase is extracted three times using 250 ml of chloroform each time. After concentrating and drying the crude product under a high vacuum, sublimation is carried out at from 70 to 90° C. and 0.2 mbar, yielding 4-chloro-2-cyanopyridine in the form of a yellowish solid.

$^1$H-NMR (360 MHz, CDCl$_3$): 8.64 (d, 5.0 Hz, 1H); 7.72 (d, J=1.8 Hz, 1H); 7.56 (dd, J=5.0, 1.8 Hz, 1H).

EXAMPLE 8

2-Amidino-4-chloropyridine hydrochloride

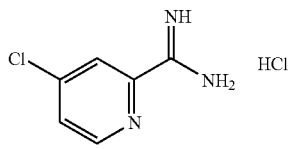

6.93 g (50 mmol) of 4-chloro-2-cyanopyridine in 40 ml of methanol are treated for one hour with 0.27 g (5 mmol) sodium methoxide. After the addition of 3.00 g (56 mmol) of ammonium chloride, refluxing is carried out for two hours. The volatile components are then removed in vacuo. The 2-amidino-4-chloropyridine hydrochloride so obtained is reacted without further purification.

$^1$H-NMR (360 MHz, D$_2$O): 8.61-8.57 (dm, 1H); 8.05 (s, 1H); 7.77-7.80 (m, 2H).

EXAMPLE 9

2,6-Bis(4-chloropyrid-2-yl)-pyrimidin-4-ol (Ligand PM5)

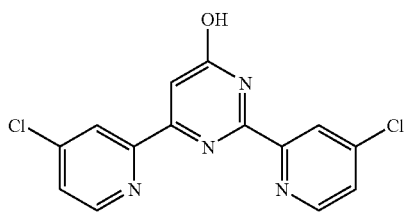

The procedure is as described in the case of 6-(4-chloropyrid-2-yl)-2-pyrid-2-yl-pyrimidin-4-ol (ligand PM1) in Example 3 except that, instead of 2-amidinopyridine hydrochloride, the 2-amidino-4-chloropyridine hydrochloride from Example 8 is used. After recrystallisation from DMSO, 2,6-bis(4-chloropyrid-2-yl)-pyrimidin-4-ol (ligand PM5) is obtained in the form of a colourless solid. $^1$H-NMR (360 MHz, DMSO-d$_6$): 12.53 (br s, 1H); 8.74 (d, J=5.0 Hz, 1H); 8.74 (s, 1H); 8.71 (d, J=5.0 Hz, 1H); 8.64 (d, J=2.3 Hz, 1H); 7.83 (dd, J=5.0, 2.3 Hz, 1H); 7.71 (dd, J=5.0, 2.3 Hz, 1H).

EXAMPLE 10

2,6-Bis[4-(4-methyl-piperazin-1-yl)-pyrid-2-yl]-pyrimidin-4-ol (Ligand PM6)

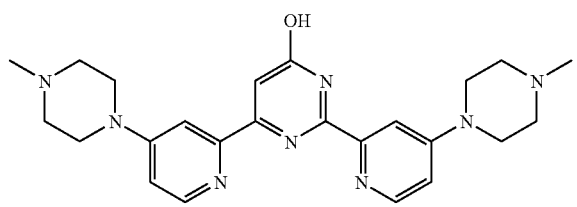

A mixture of 1.16 g (3.62 mmol), 8.04 ml (72 mmol) of N-methylpiperazine, 25 mg of zinc(II) chloride and 36 ml of 2-methyl-2-butanol is refluxed for 16 hours, cooled and filtered, and recrystallisation from 2-propanol is carried out. 2,6-Bis[4-(4-methyl-piperazin-1-yl)-pyrid-2-yl]-pyrimidin-4-ol (ligand PM6) is obtained in the form of a yellowish solid.

$^1$H-NMR (360 MHz, DMSO-d$_6$): 11.92 (br s, 1H); 8.31 (d, J=5.9 Hz, 1H); 8.30 (d, J=5.9 Hz, 1H); 7.94 (br s, 2H); 7.16 (s, 1H); 7.08 (dd, J=6.3, 2.7 Hz, 1H); 6.95 8 (dd, J=6.3, 2.7 Hz, 1H); 3.52-3.41 (m, 8H); 2.54-2.49 (m, 4H); 2.48-2.43 (m, 4H); 2.24 (s, 6H).

EXAMPLE 11

Quaternisation of 2,6-bis[4-(4-methyl-piperazin-1-yl)-pyrid-2-yl]-pyrimidin-4-ol (Ligand PM6) with Methyl Iodide to Form Ligand PM7

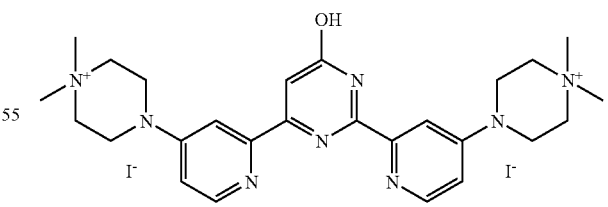

0.12 ml (1.84 mmol) of methyl iodide is added to 411 mg (0.92 mmol) of 2,6-bis[4-(4-methyl-piperazin-1-yl)-pyrid-2-yl]-pyrimidin-4-ol (ligand PM6) from Example 10 in 18 ml of acetonitrile. The mixture is stirred for 16 hours at room temperature and filtered, and the residue is washed with chloroform. The quaternised ligand PM7 is obtained in the form of a colourless solid.

$^1$H-NMR (360 MHz, D$_2$O): 8.25 (d, J=6.3 Hz, 1H); 8.19 (d, J=5.9 Hz, 1H); 7.78 (d, J=2.7 Hz, 1H); 7.50 (d, J=2.3 Hz, J=1H); 7.05 (dd, J=6.3 Hz, 2.7 Hz, 1H); 6.92 (dd, J=5.8 Hz, 2.3 Hz, 1H); 6.89 (s, 1H); 3.88-3.83 (tm, 4H); 3.81-3.76 (tm, 4H); 3.66-3.61 (m, 8H); 2.30 (s, 3H); 2.28 (s, 3H).

Synthesis of Compounds of the Triazine Type

EXAMPLE 12

4,6-Di-pyrid-2-yl-[1,3,5]triazin-2-ol (Ligand TZ1)

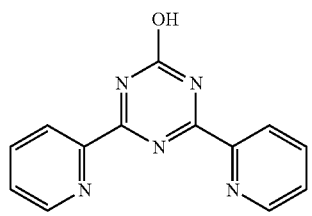

1.0 g (approximately 60% dispersion in paraffin oil, about 25 mmol) of sodium hydride is added in portions to a solution of 5.21 g (50 mmol) of 2-cyanopyridine and 1.50 g (25 mmol) of urea in 100 ml of dimethyl sulfoxide. The resulting suspension is maintained at room temperature for 3 hours and then heated at 75° C. for 23 hours, cooled and poured into 100 ml of ice-water. The mixture is rendered neutral with 2N sulfuric acid, and the crude product is filtered off and recrystallised from 55 ml of methanol, yielding 4,6-di-pyrid-2-yl-[1,3,5]triazin-2-ol in the form of a white solid.

$^1$H-NMR (360 MHz, CD$_3$OD): 8.68-8.6 (m, 4H); 7.95 (ddd, J=7.7,7.7,1.8 Hz, 2H); 7.50 (ddd, J=7.7,4.5,1.4 Hz, 2H).

EXAMPLE 13

4,6-Di-pyrid-2-yl-[1,3,5]triazin-2-ylamine (Ligand TZ2)

Synthesis according to F. H. Case et al., J. Am. Chem. Soc. 1959, 81, 905-906.

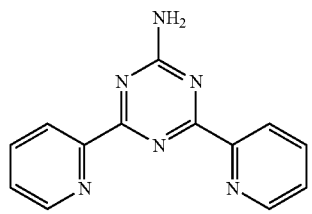

1.0 g (approximately 60% dispersion in paraffin oil, about 25 mmol) of sodium hydride is added in portions to a mixture of 5.21 g (50 mmol) of 2-cyanopyridine and 2.39 g (25 mmol) of guanidine hydrochloride in 100 ml of dimethyl sulfoxide. Stirring is carried out for 2 hours at room temperature, and then for 23 hours at 75° C. The mixture is cooled and poured into 100 ml of ice-water and filtered, yielding 4,6-di-pyrid-2-yl-[1,3,5]triazin-2-ylamine in the form of a white solid after drying in vacuo.

$^1$H-NMR (360 MHz, DMSO-d$_6$): 8.82-8.73 (md, 2H); 8.44 (d, J=8.1 Hz, 2H); 8.10-7.95 (tm, 2H); 7.90 (br s, 2H); 7.64-7.55 (m, 2H).

Synthesis of Metal Complexes

EXAMPLE 14

Manganese Complex with 6-[4-(4-methyl-piperazin-1-yl)-pyrid-2-yl]-2-pyrid-2-yl-pyrimidin-4-ol (Ligand PM2)

503 mg (2.5 mmol) of manganese chloride tetrahydrate are added to a solution of 886 mg (2.5 mmol) of 6-[4-(4-methyl-piperazin-1-yl)-pyrid-2-yl]-2-pyrid-2-yl-pyrimidin-4-ol in 200 ml of water. The solution is then freeze-dried. C$_9$H$_{20}$Cl$_2$MnN$_6$O×2.92 H$_2$O, yellow solid.

Calculated C, 43.32; H, 4.94; N, 15.95; Cl, 13.46; Mn, 10.43; H$_2$O, 9.98. found C, 43.10; H, 4.95; N, 16.03; Cl, 13.29; Mn, 10.4; H$_2$O, 9.99.

EXAMPLE 15

Manganese Complex with Quaternised 6-[4-(4-methyl-piperazin-1-yl)-pyrid-2-yl]-2-pyrid-2-yl-pyrimidin-4-ol (Ligand PM3)

119 mg (0.6 mmol) of manganese chloride tetrahydrate are added to a solution of 294 mg (0.6 mmol) of quaternised 6-[4-(4-methyl-piperazin-1-yl)-pyrid-2-yl]-2-pyrid-2-yl-pyrimidin-2-ol in 200 ml of water. The solution is then freeze-dried. C$_{20}$H$_{23}$Cl$_2$MnN$_6$O×3.75 H$_2$O, yellowish orange solid.

Calculated C, 35.13; H, 4.50; N, 12.29; Cl, 10.37; Mn, 8.03; H$_2$O, 9.88. found C, 35.38; H, 5.00; N, 12.39; Cl, 10.70; Mn, 7.99; H$_2$O, 9.87.

APPLICATION EXAMPLES

Application Example 1

Bleaching Action in Detergents 7.5 g of white cotton fabric and 2.5 g of tea-stained cotton fabric are treated in 80 ml of washing liquor. The liquor contains a standard detergent (IEC 60456 A*) in a concentration of 7.5 g/l. The hydrogen peroxide concentration is 8.6 mmol/liter. The catalyst concentration (1:1 complex of manganese(II) chloride tetrahydrate with the ligand in question, prepared in methanol or water, as described above) is 50 µmol/l. The washing processs carried out in a steel beaker in a LINITEST apparatus for 30 minutes at 40° C. To evaluate the bleaching results, the increase in lightness DY (difference in lightness according to CIE) of the stains brought about by the treatment is determined spectrophotometrically in comparison with values obtained without the addition of catalyst; see Table 1.

TABLE 1

| Mn complex with | DY increase |
| --- | --- |
| ligand PM2 | 5.3 |
| ligand PM3 | 7.4 |
| ligand PM4 | 3.8 |
| ligand TZ1 | 1.1 |
| ligand TZ2 | 1.2 |

The clear increase in lightness compared with the catalyst-free washing process (DY=0) can be seen from the Examples.

Application Example 2

Cleaning Performance on Soiled Surfaces

A filter paper stained with melanin, a pigment typically responsible for the inherent colour of mould, is welted at room temperature with a solution containing 0.4% sodium hydrogen carbonate, 0.5% sodium carbonate, 0.2% of a non-ionic surfactant (fatty alcohol polyethylene glycol ether), 2% hydrogen peroxide and, as desired, 100 ppm of a catalyst, prepared as described in Application Example 1. After 20 minutes, the filter paper is washed with water and dried at room temperature. The lightness Y of the filter paper before and after the test is determined by means of reflectance spectroscopy (according to CIE) and the bleaching performance is determined as the difference between the two measurements (DY) (Table 2). In order to assess the bleaching performance of the catalysts, a control experiment is carried out with the above-mentioned solution but without catalyst.

TABLE 2

| Catalyst | DY |
| --- | --- |
| $H_2O_2$ only | 17.5 |
| with Mn ligand PM2 | 49.7 |
| with Mn ligand PM3 | 49.6 |

The results show that the bleaching performance of hydrogen peroxide can be substantially increased by using a catalyst according to the invention.

Application Example 3

Catalysed Bleaching with Oxygen of Morin in Solution

A catalyst solution (10 µM Mn complex of Mn(II) chloride tetrahydrate with the ligand in question in methanol or water, as described above) is added at time t=0 to a solution of 160 µM morin in 10 mM carbonate buffer (pH 10). The extinction of the solution, transferred to a thermostatically controllable vessel equipped with a stirring device, is measured at 40° C. at a wavelength of 410 nm over a period of 50 min. The values for the decoloration after a test duration of 5 min. are indicated as percentages in Table 3:

TABLE 3

| Test with | Extent of the decoloration after 5 min (%) |
| --- | --- |
| Mn ligand PM2 | 49 |
| Mn ligand PM3 | 34 |
| without catalyst | 8 |
| without catalyst, with 10 mM $H_2O_2$ | 13 |

It can be seen that the bleaching action of the substances according to the invention is superior to the value of the reference (system without catalyst) and to that of 10 mM hydrogen peroxide alone.

Application Example 4

Catalytic Bleaching of Cellulose 20 g of cellulose [TMP-CT CSF129, Ref. No. P-178635 (ISO 57.4)] are steeped in a liter of water for 41 hours and then stirred in a mixer for 2 minutes to give a paste-like pulp. A bleaching bath containing 50 g of the pulp so prepared in 190 ml of aqueous buffer (49 g/liter of sodium carbonate) and in addition 10 mM hydrogen peroxide and, as desired, 2 µM manganese catalyst with ligand PM2 (prepared as described above) is maintained at 23° C. for 30 minutes. Filtration and air-drying for 3 hours are then carried out. A sample that has been compressed to form a circular sheet of 10 cm diameter is then tested for the lightness Y obtained (according to CIE, reflectance spectroscopy). The results are compiled in the following Table 4.

TABLE 4

Lightness measurement of the cellulose sample of various systems

| with peroxide | with peroxide and catalyst |
| --- | --- |
| 64.1 | 65.6 |

It is clear from Table 4 that lighter-coloured cellulose samples are obtained using the catalytic bleaching system.

Application Example 5

Catalytic Lignin-bleaching in Solution

Three glass beakers are charged with different lignin-containing mixtures:
System 1, containing:
    200 ml of test solution containing 0.1M carbonate buffer (pH 10) and alkali metal/lignin solution (Aldrich No. 37,095-9; 5 ml of a 10 g/l solution).
System 2, containing, in addition, 20 mM hydrogen peroxide solution.
System 3, as system 2 but containing, in addition, 10 µM manganese catalyst with ligand PM2, prepared as described above.

The absorption at 425 nm wavelength is determined spectrophotometrically, after 35 minutes, as a measure of the bleaching activity of the system in question.

TABLE 5

Absorption measurement at 425 nm

| System 1 | System 2 | System 3 |
| --- | --- | --- |
| 0.523 | 0.479 | 0.454 |

It can be seen from Table 5 that the catalytic system 3 has a better lignin-bleaching action than the catalyst-free systems 1 and 2.

Application Example 6

Delignification of Pulp 5 g (dry weight) of softwood cellulose having a Kappa number of 26.4 are introduced with 71 ml of carbonate buffer, pH 10 (0.4% sodium hydrogen carbonate and 0.5% sodium carbonate) and 13.3 ml of 30% hydrogen peroxide solution into a plastic bag. The catalyst solution is prepared in advance by mixing an aqueous solution of an equimolar mixture of iron(III) chloride and the ligand PM2. 53.2 ppm of the catalyst are added to the pulp. The pulp so obtained is kneaded intensively and then maintained at 40° C. under thermostatic control for 90 min. in a water bath.

Filtration is then carried out and the pulp is washed three times with hot water (60° C.). The Kappa number of the pulp after the treatment is determined according to TAPPI T236 om-99 and is 17.5. The Kappa number of the pulp in a control experiment without catalyst is 19.6. The use of the catalyst thus results in a further reduction of the Kappa number.

Application Example 7

Action as a Catalyst for Dye Transfer Inhibition (DTI)

According to this application, the object is to prevent redeposition of migrating dyes, especially in washing liquors.

7.5 g of white cotton fabric are treated in 80 ml of washing liquor. The liquor comprises a standard detergent (IEC 60456 A*) in a concentration of 7.5 g/l, 8.6 mmol/l of hydrogen peroxide and a solution of the test dye Reactive Blue 238 (6 mg/l of the 100% formulation). The catalyst solution is prepared in advance by mixing an aqueous solution of manganese(II) chloride tetrahydrate or iron(II) chloride and the appropriate ligand. There is thus established a catalyst concentration of 50 μmol/l in the liquor. The washing process is carried out for 30 minutes at 40° C. in a steel beaker in a LINITEST apparatus. To test the activity of the catalysts, the DTI activity is determined. The DTI (dye transfer inhibition) activity a is defined as the following percentage:

$$a=([Y(E)-Y(A)]/[Y(W)-Y(A)])*100$$

wherein Y(W), Y(A) and Y(E) are the CIE lightness values of the white material, of the material treated without the addition of catalyst and of the material treated with the addition of catalyst (in that order). a=100% corresponds to a perfect catalyst which totally prevents the staining of the white material.

The reflection spectra of the samples are measured using a SPECTRAFLASH 2000 and converted into lightness values (D65/10) in accordance with a standard CIE procedure. The results are shown in Table 6 below.

TABLE 6

| Test with | DTI effect a |
|---|---|
| Mn ligand PM2 | 20% |
| Mn ligand PM3 | 32% |
| Fe ligand PM2 | 99% |
| Fe ligand PM3 | 99% |

The ability of the catalysts to inhibit dye transfer is clear from Table 6.

What is claimed is:

1. A detergent, cleaning, disinfecting or bleaching composition containing

I) from 0 to 50% A) of an anionic surfactant and/or B) of a non-ionic surfactant, II) from 0 to 70% C) of a builder substance, III) from 1 to 99% D) of a peroxide selected from the group consisting of organic peroxides and inorganic peroxides, IV) E) from 0.005 to 2% of at least one metal complex compound of formula (1a)

$$[L_nMe_mX_p]^zY_q \qquad (1a)$$

wherein

Me is manganese, titanium, iron, cobalt, nickel or copper

X is a coordinating or bridging radical n and m are each independently of the other an integer having a value of from 1 to 8 p is an integer having a value of from 0 to 32, z is the charge of the metal complex Y is a counter-ion q=z/(charge of Y), and L is a ligand of formula (2)

(2)

wherein

Q is N or $CR_{10}$ $R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$; —$SR_{12}$, —$SO_2R_{12}$ or —$OR_{12}$; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—N—$R_{13}R_{14}$ or —$N(R_{12})$—$N^{\oplus}R_{13}R_{14}R_{15}$, wherein $R_{11}$ is in each case hydrogen a cation or unsubstituted or substituted $C_1$-$C_{18}$alkyl or unsubstituted or substituted aryl, $R_{12}$ is in each case hydrogen or unsubstituted or substituted $C_1$-$C_{18}$alkyl or unsubstituted or substituted aryl, and $R_{13}$, $R_{14}$ and $R_{15}$ are each independently of the other(s) hydrogen or unsubstituted or substituted $C_1$-$C_{18}$alkyl or unsubstituted or substituted aryl or $R_{13}$ and $R_{14}$, together with the nitrogen atom linking them, form an unsubstituted or substituted 5-, 6- or 7-membered ring which may contain further hetero atoms, the percentages in each case being percentages by weight, based on the total weight of the composition, and V) water ad 100%.

2. A solid formulation containing a) from 1 to 99% by weight of a metal complex compound of formula (1a), $$[L_nMe_mX_p]^zY_q \qquad (1a)$$

wherein
Me is manganese, titanium, iron, cobalt, nickel or copper
X is a coordinating or bridging radical
n and m are each independently of the other an integer having a value of from 1 to 8
p is an integer having a value of from 0 to 32
z is the charge of the metal complex
Y is a counter-ion
q=z/(charge of Y), and
L is a ligand of formula (2)

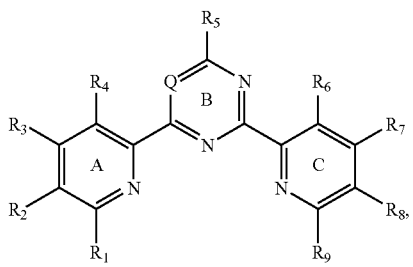

wherein
Q is N or $CR_{10}$
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$; —$SR_{12}$, —$SO_2R_{12}$ or —$OR_{12}$; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—N—$R_{13}R_{14}$ or —$N(R_{12})$—$N^{\oplus}R_{13}R_{14}R_{15}$, wherein
$R_{11}$ is in each case hydrogen a cation or unsubstituted or substituted $C_1$-$C_{18}$alkyl or unsubstituted or substituted aryl,
$R_{12}$ is in each case hydrogen or unsubstituted or substituted $C_1$-$C_{18}$alkyl or unsubstituted or substituted aryl, and
$R_{13}$, $R_{14}$ and $R_{15}$ are each independently of the other(s) hydrogen or unsubstituted or substituted $C_1$-$C_{18}$alkyl or unsubstituted or substituted aryl, or
$R_{13}$ and $R_{14}$, together with the nitrogen atom linking them, form an unsubstituted or substituted 5-, 6- or 7-membered ring which may contain further hetero atoms,
b) from 1 to 99% by weight of a binder selected from the group consisting of water-soluble, dispersible or water-emulsifiable anionic dispersants, nonionic dispersants, and waxes,
c) from 1 to 20% by weight of an encapsulating material selected from the group consisting of water-soluble, water-dispersible or water-emulsifiable polymers and waxes,
d) from 0 to 20% by weight of a further additive and
e) from 0 to 20% by weight of water.

3. A solid formulation according to claim 2, which is in the form of tablets or granules.

4. A detergent, cleaning, disinfecting or bleaching composition containing
I) from 0 to 50% A) of an anionic surfactant and/or B) of a non-ionic surfactant,
II) from 0 to 70% C) of a builder substance,
III) from 1 to 99% D) of a peroxide selected from the group consisting of organic peroxides and inorganic peroxides,
IV) E) from 0.005 to 2% of at least one metal complex compound of formula (1'a)

$$[L'_n Me_m X_p]^z Y_q \qquad (1'a)$$

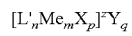

wherein
Me is manganese, titanium, iron, cobalt, nickel or copper
X is a coordinating or bridging radical
n and m are each independently of the other an integer having a value of from 1 to 8
p is an integer having a value of from 0 to 32
z is the charge of the metal complex
Y is a counter-ion
q=z/(charge of Y), and
L' is a ligand of formula (2')

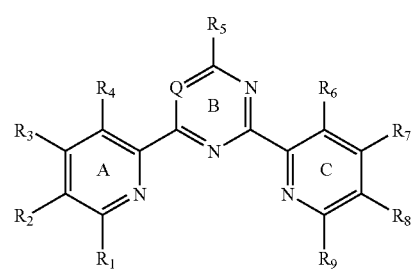

wherein
Q is N or $CR_{10}$
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$; —$SR_{12}$, —$SO_2R_{12}$ or —$OR_{12}$; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—N—$R_{13}R_{14}$ or —$N(R_{12})$—$N^{\oplus}R_{13}R_{14}R_{15}$, wherein
$R_{11}$ is in each case hydrogen, a cation or unsubstituted or substituted $C_1$-$C_{18}$alkyl or substituted or unsubstituted aryl
$R_{12}$ is in each case hydrogen or unsubstituted or substituted $C_1$-$C_{18}$alkyl or unsubstituted or substituted aryl and
$R_{13}$, $R_{14}$ and $R_{15}$ are each independently of the other(s) hydrogen or unsubstituted or substituted $C_1$-$C_{18}$alkyl or unsubstituted or substituted aryl or
$R_{13}$ and $R_{14}$, together with the nitrogen atom linking them, form an unsubstituted or substituted 5-, 6- or 7-membered ring which may contain further hetero atoms with the proviso that
at least one of the substituents $R_1$ to $R_{10}$ contains a quaternised nitrogen atom that is not bonded directly to one of the three rings A, B and/or C, the percentages in each case being percentages by weight, based on the total weight of the composition, and V) water ad 100%.

5. A solid formulation containing
a) from 1 to 99% by weight of a metal complex compound of formula (1'a)

$$[L'_n Me_m X_p]^z Y_q \quad (1'a)$$

wherein
Me is manganese, titanium, iron, cobalt, nickel or copper
X is a coordinating or bridging radical
n and m are each independently of the other an integer having a value of from 1 to 8
p is an integer having a value of from 0 to 32
z is the charge of the metal complex
Y is a counter-ion
q=z/(charge of Y) and
L' is a ligand of formula (2')

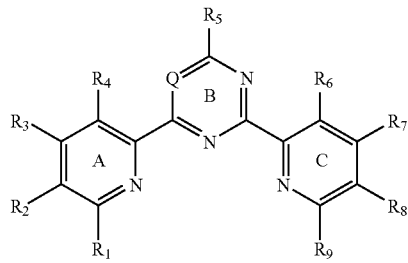

wherein
Q is N or $CR_{10}$
$R_1$, $R_2$, $R_3$, $R_4$, $R_5$, $R_6$, $R_7$, $R_8$, $R_9$ and $R_{10}$ are each independently of the others hydrogen; unsubstituted or substituted $C_1$-$C_{18}$alkyl or unsubstituted or substituted aryl; cyano; halogen; nitro; —$COOR_{11}$ or —$SO_3R_{11}$; —$SR_{12}$, —$SO_2R_{12}$ or —$OR_{12}$; —$NR_{13}R_{14}$; —($C_1$-$C_6$alkylene)—$NR_{13}R_{14}$; —$N^{\oplus}R_{13}R_{14}R_{15}$; —($C_1$-$C_6$alkylene)—$N^{\oplus}R_{13}R_{14}R_{15}$; —$N(R_{12})$—($C_1$-$C_6$alkylene)—$NR_{13}R_{14}$; —$N[(C_1$-$C_6$alkylene)—$NR_{13}R_{14}]_2$; —$N(R_{12})$—($C_1$-$C_6$alkylene)—$N^{\oplus}R_{13}R_{14}R_{15}$; —$N[(C_1$-$C_6$alkylene)—$N^{\oplus}R_{13}R_{14}R_{15}]_2$; —$N(R_{12})$—$N$—$R_{13}R_{14}$ or —$N(R_{12})$—$N^{\oplus}R_{13}R_{14}R_{15}$, wherein $R_{11}$ is in each case hydrogen, a cation or unsubstituted or substituted $C_1$-$C_{18}$alkyl or substituted or unsubstituted aryl $R_{12}$ is in each case hydrogen or unsubstituted or substituted $C_1$-$C_{18}$alkyl or unsubstituted or substituted aryl and $R_{13}$, $R_{14}$ and $R_{15}$ are each independently of the other(s) hydrogen or unsubstituted or substituted $C_1$-$C_{18}$alkyl or unsubstituted or substituted aryl, or $R_{13}$ and $R_{14}$, together with the nitrogen atom linking them, form an unsubstituted or substituted 5-, 6- or 7-membered ring which may contain further hetero atoms with the proviso that at least one of the substituents $R_1$ to $R_{10}$ contains a quaternised nitrogen atom that is not bonded directly to one of the three rings A, B and/or C, b) from 1 to 99% by weight of a binder selected from the group consisting of water-soluble, dispersible or water-emulsifiable anionic dispersants, nonionic dispersants, and waxes, c) from 1 to 20% by weight of an encapsulating material selected from the group consisting of water-soluble, water-dispersible or water-emulsifiable polymers and waxes, d) from 0 to 20% by weight of a further additive and e) from 0 to 20% by weight of water.

6. A solid formulation according to claim 5, which is in the form of tablets or granules.

* * * * *